United States Patent [19]

Ohishi et al.

[11] Patent Number: 5,350,743

[45] Date of Patent: Sep. 27, 1994

[54] BISPHOSPHONIC ACID DERIVATIVES, AS BONE RESORPTION INHIBITORS

[75] Inventors: Yoshitaka Ohishi; Makoto Tamura; Mitsuo Hayashida; Satoru Ikegami; Yoshiyuki Hiyama; Takao Awa; Kiyonoshin Ichikawa; Kiyoshi Nomiyama; Keigo Hanada; Mitsuo Mimura, all of Kyoto, Japan

[73] Assignee: Kaken Pharmaceutical Co., Ltd., Tokyo, Japan

[21] Appl. No.: 831,965

[22] Filed: Feb. 6, 1992

[30] Foreign Application Priority Data

Feb. 7, 1991 [JP] Japan .................. 3-016640
Aug. 1, 1991 [JP] Japan .................. 3-193050

[51] Int. Cl.$^5$ ............ C07F 9/59; A61K 31/675
[52] U.S. Cl. ....................... 514/89; 514/91; 514/278; 546/16; 546/32; 548/407; 548/513; 548/514
[58] Field of Search .............. 514/89; 546/22

[56] References Cited

U.S. PATENT DOCUMENTS 3,846,420 11/1974 Wollmann et al. ............. 544/157
3,899,496 8/1975 Schindler et al. ............... 546/22

FOREIGN PATENT DOCUMENTS 0325482 7/1989 European Pat. Off. ......... 562/13
WO8703598 6/1987 PCT Int'l Appl. ............ 514/79

OTHER PUBLICATIONS

Chemical Abstracts, vol. 89(23) Abst. No. 197,715d, Dec. 04, 1978.
Chemical Abstracts, vol. 92(17) Abst. No. 146,905v, Apr. 28, 1980.

*Primary Examiner*—Alan L. Rotman
*Attorney, Agent, or Firm*—Oblon, Spivak, McClelland, Maier & Neustadt

[57] ABSTRACT

A bisphosphonic acid derivative of the formula (I) or a pharmaceutically acceptable salt thereof:

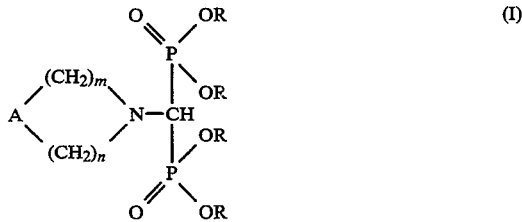

wherein A is

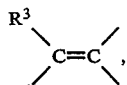

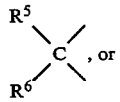

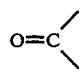

each of $R^3$ and $R^4$, which may be the same or different, is (i) a hydrogen atom, (ii) a $C_{1-6}$ alkyl group, a $C_{2-6}$ alkenyl group, a $C_{2-6}$ alkynyl group, a $C_{1-6}$ alkyl-carbonyl group, a $C_{2-6}$ alkenyl-carbonyl group, a $C_{2-6}$ alkynyl-carbonyl group $R^5$ and $R^6$, which may be the same or different, is a hydrogen atom, a hydroxyl group, a halogen atom, a cyano group, a carbamoyl group, an aralkyl group, a substituted or unsubstituted phenyl group, a substituted or unsubstituted amino group, a $C_{1-6}$ alkyl group, a $C_{2-6}$ alkenyl group, a $C_{2-6}$ alkynyl group;

each of m and n is 0 or a positive integer, provided that (m+n) is from 2 to 5; and R is a hydrogen atom, a $C_{1-8}$ alkyl group or a $C_{7-15}$ aralkyl group.

10 Claims, No Drawings

BISPHOSPHONIC ACID DERIVATIVES, AS BONE RESORPTION INHIBITORS

The present invention relates to bisphosphonic acid derivatives, their intermediates and bone resorption inhibitors containing them as active ingredients.

Osteoporosis has become a serious problem as the population of old men and women has increased. Heretofore, it has been common to employ, as a treating method, a method of administering calcium to increase the calcium concentration in the body. However, such a method is not essentially effective for treating osteoporosis. Therefore, it is desired to develop a new drug for treating osteoporosis. Japanese Unexamined Patent Publication No. 30829/1989 discloses a cycloalkylaminomethylene bisphosphonic acid as one type of bisphosphonic acid, and it is described that this compound has a bone resorption inhibiting activity and thus is effective for treating osteoporosis. However, such a bisphosphonic acid has a drawback that it has a strong local irritating activity, and it shows a side effect such that when subcutaneously injected, it leads to inflammation of the skin.

It is therefore an object of the present invention to provide a compound which has a bone resorption inhibiting activity and no substantial side effect and which is thus useful as a drug for treating a bone disease such as osteoporosis.

The present invention provides a bisphosphonic acid derivative of the formula (I) or a pharmaceutically acceptable salt thereof:

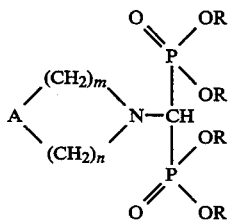

wherein A is

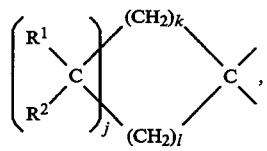

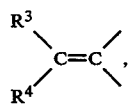

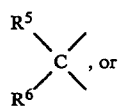

wherein each of $R^1$ and $R^2$, which may be the same or different, is a hydrogen atom, a halogen atom, a $C_{1-6}$ alkyl group or a single bond, each of j, k and l is 0 or a positive integer, provided that (j+k+l) is from 2 to 6, each of $R^3$ and $R^4$, which may be the same or different, is (i) a hydrogen atom, (ii) a $C_{1-6}$ alkyl group, a $C_{2-6}$ alkenyl group, a $C_{2-6}$ alkynyl group, a $C_{1-6}$ alkyl-carbonyl group, a $C_{2-6}$ alkenyl-carbonyl group, a $C_{2-6}$ alkynyl-carbonyl group (these groups may be substituted by at least one member selected from the group consisting of a substituted amino group, a halogen atom and a carboxyl group), or (iii) a halogen atom, each of $R^5$ and $R^6$, which may be the same or different, is a hydrogen atom, a hydroxyl group, a halogen atom, a cyano group, a carbamoyl group, an aralkyl group, a substituted or unsubstituted phenyl group, a substituted or unsubstituted amino group, a $C_{1-6}$ alkyl group, a $C_{2-6}$ alkenyl group, a $C_{2-6}$ alkynyl group or a heterocyclic group having a nitrogen atom as the hetero atom, provided that when either one of $R^5$ and $R^6$ is a hydrogen atom, the other is other than a hydrogen atom or a $C_{1-6}$ alkyl group;

each of m and n is 0 or a positive integer, provided that (m+n) is from 2 to 5; and R is a hydrogen atom, a $C_{1-8}$ alkyl group or a $C_{7-15}$ aralkyl group.

In this specification, the compound of the present invention refers generally to the bisphosphonic acid derivative of the formula (I) and its pharmaceutically acceptable salt.

Now, the present invention will be described in detail with reference to the preferred embodiments.

In the formula (I), R is a hydrogen atom, a $C_{1-8}$ alkyl group or a $C_{7-15}$ aralkyl group. Here, the $C_{1-8}$ alkyl group may be a linear or branched alkyl group such as a methyl group, an ethyl group, a propyl group, a butyl group, a pentyl group, a hexyl group, a heptyl group or an octyl group. The $C_{7-15}$ aralkyl group may, for example, be a benzyl group, a phenylethyl group, a methylbenzyl group or a naphthylmethyl group.

Four R groups in the formula (I) may be the same or different groups. However, the four R groups are preferably the same, for example, for the convenience in synthesis.

Each of m and n is 0 or a positive integer, provided that (m+n) is from 2 to 5. If (m+n) is 1 or less, the ring will be 3- or less-membered, and if (m+n) is 6 or more, the ring will be 8- or more-membered. In either case, the synthesis will be difficult.

When A in the formula (I) is

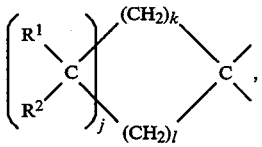

each of $R^1$ and $R^2$ is a hydrogen atom, a halogen atom, a $C_{1-6}$ alkyl group or a single bond. Here, the $C_{1-6}$ alkyl group may be a methyl group, an ethyl group, a n-propyl group, an iso-propyl group, a n-butyl group, an iso-butyl group or a tert-butyl group. The halogen atom may be fluorine, chlorine, bromine or iodine. $R^1$ and $R^2$ may be the same or different.

Each of j, k and l is 0 or a positive integer, provided that (j+k+l) is from 2 to 6. If (j+k+l) is 1 or less, no ring can be formed, and if (j+k+l) is 7 or more, the ring will be 8- or more-membered, and the synthesis will be difficult.

PROCESS 1

A derivative of the formula (I) wherein A is

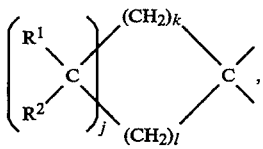

wherein R is a $C_{1-8}$ alkyl group or a $C_{7-15}$ aralkyl group, can be prepared by the following process.

Namely, it can be obtained by reacting a compound of the formula (II):

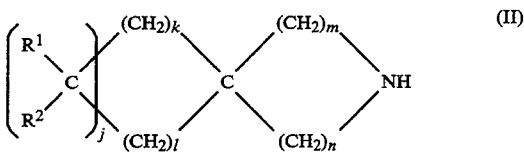 (II)

wherein $R^1$, $R^2$, j, k, l, m and n are as defined above, with a compound of the formula (III):

(R'O)$_2$PHO        (III)

wherein R' is a $C_{1-8}$ alkyl group or a $C_{7-15}$ aralkyl group, and a compound of the formula (IV):

HC(OR$^7$)$_3$        (IV)

wherein $R^7$ is a $C_{1-3}$ alkyl group. Here, the $C_{1-3}$ alkyl group for $R^7$ may be a methyl group, an ethyl group, a linear or branched propyl group. In this reaction, it is preferred to employ from 2 to 50 equivalent mols of the compound of the formula (III) and from 1 to 3 equivalent mols of the compound of the formula (IV), per mol of the compound of the formula (II). The reaction temperature is preferably from 100° to 200° C., and the reaction time is preferably from 5 to 100 hours.

When A in the formula (I) is

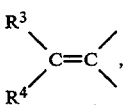

each of $R^3$ and $R^4$, which may be the same or different, is (i) a hydrogen atom, (ii) a $C_{1-6}$ alkyl group, a $C_{2-6}$ alkenyl group, a $C_{2-6}$ alkynyl group, a $C_{1-6}$ alkyl-carbonyl group, a $C_{2-6}$ alkenyl-carbonyl group, a $C_{2-6}$ alkynyl-carbonyl group (these groups may be substituted by at least one member selected from the group consisting of a substituted amino group, a halogen atom and a carboxyl group), or (iii) a halogen atom.

Here, the $C_{1-6}$ alkyl group may, for example, be a methyl group, an ethyl group, a n-propyl group, an isopropyl group, a n-butyl group, a branched butyl group, a n-pentyl group, a branched pentyl group, a n-hexyl group or a branched hexyl group. The $C_{2-6}$ alkenyl group is a linear or branched alkenyl group having at least one double bond, and as such an alkenyl group, a vinyl group, an allyl group, a 1-methylvinyl group, a 2-methylvinyl group, a 1-ethylvinyl group, a 2-ethylvinyl group, a 2,2-dimethylvinyl group, a 3-methylallyl group, a 2-vinylvinyl group or a 2-butylvinyl group may, for example, be mentioned. The $C_{2-6}$ alkynyl group is a linear or branched alkynyl group having at least one triple bond, and as such an alkynyl group, an ethynyl group, 1-propynyl group, a 1-butynyl group, a 1-heptynyl group, a 1-isoheptynyl group or a 2-propynyl group may, for example, be mentioned. The $C_{1-6}$ alkyl-carbonyl group is a group having a carbonyl group bonded to the above $C_{1-6}$ alkyl group. Likewise, the $C_{1-6}$ alkenyl-carbonyl group is a group having a carbonyl group bonded to the above $C_{2-6}$ alkenyl group, and the $C_{2-6}$ alkynyl-carbonyl group is a group having a carbonyl group bonded to the above $C_{2-6}$ alkynyl group.

Such alkyl, alkenyl, alkynyl, alkyl-carbonyl, alkenyl-carbonyl and alkynyl-carbonyl groups (hereinafter sometimes referred to generally as the groups of Group (ii)) may be substituted by at least one member selected from the group consisting of a substituted amino group, a halogen atom and a carboxyl group. Here, the substituted amino group which may be substituted on the groups of Group (ii) may, for example, be a dialkylamino group such as a dimethylamino group, a diethylamino group or a dipropylamino group, or a dialkanolamino group such as a dimethanolamino group or a diethanolamino group. As the halogen atom which may be substituted on the groups of Group (ii), fluorine, bromine, iodine or chlorine may be mentioned.

Further, $R^3$ and/or $R^4$ may be the above-mentioned halogen atom.

$R^3$ and $R^4$ as described above, may be the same or different.

PROCESS 2

A derivative of the formula (I) wherein A is

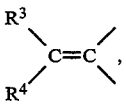

and R is a $C_{1-8}$ alkyl group or a $C_{7-15}$ aralkyl group, can be prepared by the following process.

Namely, it can be obtained by reacting a compound of the formula (V):

 (V)

wherein $R^3$, $R^4$, m and n are as defined above, with a compound of the formula (III):

(R'O)$_2$PHO        (III)

wherein R' is as defined above, and a compound of the formula (IV):

HC(OR$^7$)$^3$        (IV)

wherein $R^7$ is as defined above.

In this reaction, it is preferred to employ from 2 to 50 mols of the compound of the formula (III) and from 1 to 3 equivalent mols of the compound of the formula (IV), per mol of the compound of the formula (V). The reaction temperature is preferably from 100° to 200° C., and the reaction time is preferably from 5 to 100 hours.

Instead of the compound of the formula (V), an inorganic salt or organic salt thereof may be employed. In such a case, it is preferred to employ from 1.2 to 3.5 equivalent mols of an organic base per mol of the acid salt of the compound of the formula (V) in addition to the compounds of the formulas (III) and (IV).

PROCESS 3

A derivative of the formula (I) wherein A is

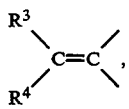

and R is a $C_{1-8}$ alkyl group or a $C_{7-15}$ aralkyl group, can also be produced by the following process.

Namely, it can be obtained by reacting a wittig reagent of the formula (VII):

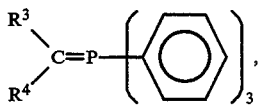

wherein $R^3$ and $R^4$ are as defined above, to the compound of the formula (VI):

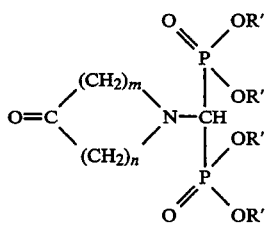

(VI)

wherein R', m and n are as defined above When A in the formula (I) is

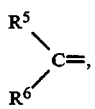

each of $R^5$ and $R^6$, which may be the same or different, is a member selected from the group consisting of a hydrogen atom, a hydroxyl group, a halogen atom, a cyano group, a carbamoyl group, an aralkyl group, a substituted or unsubstituted phenyl group, a substituted or unsubstituted amino group, a $C_{1-6}$ alkyl group, a $C_{2-6}$ alkenyl group, a $C_{2-6}$ alkynyl group and a heterocyclic group having a nitrogen atom as the hetero atom.

Namely, each of $R^5$ and $R^6$ may be the following group or atom:

(i) a hydrogen atom, a hydroxyl group, a halogen atom, a cyano group, a carbamoyl group, (ii) an aralkyl group such as a benzyl group or a phenylethyl group, (iii) a substituted or unsubstituted phenyl group (the substituent may, for example, be a lower alkyl group, a hydroxyl group, a halogen atom, a lower alkylamino group or a carboxy group), (iv) a substituted or unsubstituted amino group (the substituent may, for example, be a dialkyl group such as a dimethyl group, a diethyl group or a dipropyl group, or a dialkanol group such as a dimethanol group or a diethanol group), (v) a $C_{1-6}$ alkyl group such as a methyl group, an ethyl group, a n-propyl group, an isopropyl group, a n-butyl group, a branched butyl group, a n-pentyl group, a branched pentyl group, a n-hexyl group or a branched hexyl group, a $C_{2-6}$ alkenyl group which is a linear or branched alkenyl group having at least one double bond, such as a vinyl group, an allyl group, a 2,2-dimethylvinyl group or a 3-methylallyl group, a $C_{2-6}$ alkynyl group which is a linear or branched alkynyl group having at least one triple bond, such as an ethynyl group or a propynyl group, (vi) a heterocyclic group having a nitrogen atom as the hetero atom, such as a pyrrolyl group, an imidazolyl group, a pyridinyl group, an imidazolynyl group, a piperidinyl group or a piperidino group.

$R^5$ and $R^6$ may be the same or different, but when either one of $R^5$ and $R^6$ is a hydrogen atom, the other is other than a hydrogen atom or a $C_{1-6}$ alkyl group.

PROCESS 4

A derivative of the formula (I) wherein A is

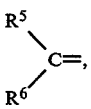

and R is a $C_{1-8}$ alkyl group or a $C_{7-15}$ aralkyl group, can be produced also by the following process.

Namely, it can be obtained by reacting a compound of the formula (VIII):

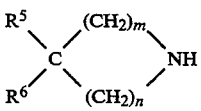 (VIII)

wherein $R^5$, $R^6$, m and N are as defined above, with a compound of the formula (III):

$(R'O)_2PHO$ (III)

wherein R' is as defined above, and a compound of the formula (IV):

$HC(OR^7)_3$ (IV)

wherein $R^7$ is as defined above. In this process, it is preferred to employ from 2 to 50 equivalent mols of the compound of the formula (III) and from 1 to 3 equivalent mols of the compound of the formula (IV), per mol of the compound of the formula (VIII). The reaction temperature is preferably from 100° to 200° C., and the reaction time is preferably from 5 to 100 hours.

PROCESS 5

A derivative of the formula (I) wherein A is

wherein either one of $R^5$ and $R^6$ is a halogen atom, and R is a $C_{1-8}$ alkyl group or a $C_{7-15}$ aralkyl group, can be produced also by the following process.

Namely, it can be obtained by reacting hydrogen halide gas such as hydrogen chloride gas to a compound of the formula (IX):

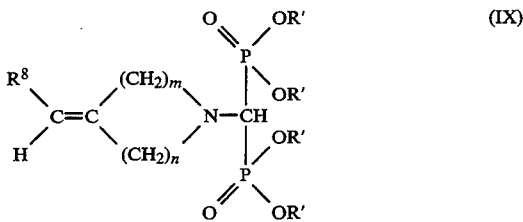

wherein R', m and n are as defined above, and $R^8$ is a hydrogen atom or a $C_{1-6}$ alkyl group.

PROCESS 6

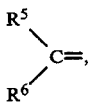

wherein either one of $R^5$ and $R^6$ is a hydroxyl group, can be obtained also by heat treating the compound of the above Process 5 in dilute sulfuric acid for hydration.

PROCESS 7

A derivative of the formula (I) wherein A is

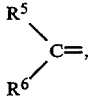

wherein either one of $R^5$ and $R^6$ is a fluorine atom, and the other is a $C_{1-6}$ alkyl group, can be obtained by stirring a 4-hydroxy-4-alkylpiperidinomethylenebisphosphonic acid alkyl ester in an inert organic solvent at room temperature together with a diethylamino sulfite triglyceride, or by reacting them with a further addition of trimethylsilyl iodide.

PROCESS 8

A derivative of the formula (I) wherein A is

can be obtained by reacting a 1,4-dioxa-8-azaspiro[4,5]-dodecane-8-methylene bisphosphonic acid alkyl ester in an aqueous acetic acid solution.

PROCESS 9

A bisphosphonic acid derivative of the formula (I) wherein R is a hydrogen atom, can be obtained by treating a bisphosphonic acid derivative of the formula (I) wherein R is a $C_{1-8}$ alkyl group or a $C_{7-15}$ aralkyl group, with hydrochloric acid, an aqueous sodium hydroxide solution, a hydrogen bromide-acetic acid mixed solution or $(CH_3)_3SiI$.

A pharmaceutically acceptable salt of the bisphosphonic acid derivative of the formula (I) is also covered by the present invention. As such a salt, an inorganic salt such as a sodium salt, a potassium salt, a magnesium salt or a calcium salt, or a salt with an amino acid such as glycine, alanine, phenylalanine or lysine, may be mentioned.

The bisphosphonic acid derivative of the formula (I) strongly suppresses bone resorption and has no local irritating activity, and thus it can effectively be used as a bone resorption inhibitor, such as an agent for treating a bone disease such as osteoporosis.

The bisphosphonic acid derivative of the present invention may be used by itself as a bone resorption inhibitor. However, it can be used in the form of various formulations which may be prepared by conventional formulation methods. For example, it can be used in the form of a formulation for oral administration such as a tablet, a powder, a capsule or a syrup, or a formulation for non-oral administration such as an injection drug or a suppository.

The dose varies depending upon the diseased condition, the age and the body weight of the patient, the therapeutic effects, the manner for administration or the period for administration. However, the compound of the present invention is usually preferably administered within a range of from 10 to 1000 mg per day for an adult in the case of oral administration.

As the bisphosphonic acid derivative of the formula (I) wherein A is

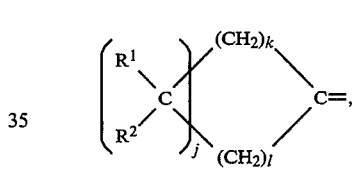

the following compounds may, for example, be mentioned.

(1) 3-azaspiro[5.5]undecan-3-yl-methylene bisphosphonic acid (2) 2-azaspiro[5.5]undecan-2-yl-methylene bisphosphonic acid (3) 2-azaspiro[5.5]undecan-8-en-2-yl--methylene bisphosphonic acid (4) 6-azaspiro[2.5]octan-6-yl-methylene bisphosphonic acid (5) 8-azaspiro[4.5]decan-8-yl-methylene bisphosphonic acid (6) 1-azaspiro[5.5]undecan-1-yl-methylene bisphosphonic acid (7) 2-azaspiro[4.5]decan-2-yl-methylene bisphosphonic acid (8) 1-azaspiro[4.5]decan-1-yl-methylene bisphosphonic acid (9) 8-azaspiro[5.6]dodecan-8-yl-methylene bisphosphonic acid

(10) 7-azaspiro[5.6]dodecan-7-yl-methylene bisphosphonic acid

(11) 2-azaspiro[3.5]nonan-2-yl-methylene bisphosphonic acid

(12) 1-azaspiro[2.6]nonan-1-yl-methylene bisphosphonic acid

(13) 8-methyl-2-azaspiro[4.5]decan-2-yl-methylene bisphosphonic acid

(14) 1,1-difluoro-6-azaspiro[2.5]octan-6-yl-methylene bisphosphonic acid

(15) bisphosphonic acid esters having the $(PO_3H_2)_2$ groups at the terminals of the above bisphosphonic acids (1) to (14) changed to $[PO(O-R)_2]_2$ groups.

Further, as the bisphosphonic acid derivative of the formula (I) wherein A is

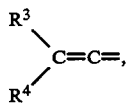

the following compounds may, for example, be mentioned.

TABLE 1

| No. | $R^3$ | $R^4$ | m | n | R |
|---|---|---|---|---|---|
| 1 | H | H | 2 | 2 | H |
| 2 | H | H | 2 | 2 | —$CH_3$ |
| 3 | H | H | 2 | 2 | —$C_2H_5$ |
| 4 | H | H | 2 | 2 | —$C_3H_7$ |
| 5 | H | H | 2 | 2 | —$CH_2$—$C_6H_5$ |
| 6 | —$CH_3$ | H | 2 | 2 | H |
| 7 | —$CH_3$ | H | 2 | 2 | —$CH_3$ |
| 8 | —$CH_3$ | H | 2 | 2 | —$C_2H_5$ |
| 9 | —$CH_3$ | H | 2 | 2 | —$C_3H_7$ |
| 10 | —$CH_3$ | H | 2 | 2 | —$CH_2$—$C_6H_5$ |
| 11 | —$CH_3$ | —$CH_3$ | 2 | 2 | H |
| 12 | —$CH_3$ | —$CH_3$ | 2 | 2 | —$CH_3$ |
| 13 | —$CH_3$ | —$CH_3$ | 2 | 2 | —$C_2H_5$ |
| 14 | —$CH_3$ | —$CH_3$ | 2 | 2 | —$C_3H_7$ |
| 15 | —$CH_3$ | —$CH_3$ | 2 | 2 | —$CH_2$—$C_6H_5$ |
| 16 | —$C_2H_5$ | H | 2 | 2 | H |
| 17 | —$C_2H_5$ | H | 2 | 2 | —$CH_3$ |
| 18 | —$C_2H_5$ | H | 2 | 2 | —$C_2H_5$ |
| 19 | —$C_2H_5$ | H | 2 | 2 | —$C_3H_7$ |
| 20 | —$C_2H_5$ | H | 2 | 2 | —$CH_2$—$C_6H_5$ |
| 21 | —$C_2H_5$ | —$C_2H_5$ | 2 | 2 | H |
| 22 | —$C_2H_5$ | —$C_2H_5$ | 2 | 2 | —$CH_3$ |
| 23 | —$C_2H_5$ | —$C_2H_5$ | 2 | 2 | —$C_2H_5$ |
| 24 | —$C_2H_5$ | —$C_2H_5$ | 2 | 2 | —$C_3H_7$ |
| 25 | —$C_2H_5$ | —$C_2H_5$ | 2 | 2 | —$CH_2$—$C_6H_5$ |
| 26 | H | H | 1 | 3 | H |
| 27 | H | H | 1 | 3 | —$CH_3$ |
| 28 | H | H | 1 | 3 | —$C_2H_5$ |
| 29 | H | H | 1 | 3 | —$C_3H_7$ |
| 30 | H | H | 1 | 3 | —$CH_2$—$C_6H_5$ |
| 31 | —$CH_3$ | H | 1 | 3 | H |
| 32 | —$CH_3$ | H | 1 | 3 | —$CH_3$ |
| 33 | —$CH_3$ | H | 1 | 3 | —$C_2H_5$ |
| 34 | —$CH_3$ | H | 1 | 3 | —$C_3H_7$ |
| 35 | —$CH_3$ | H | 1 | 3 | —$CH_2$—$C_6H_5$ |
| 36 | —$CH_3$ | —$CH_3$ | 1 | 3 | H |
| 37 | —$CH_3$ | —$CH_3$ | 1 | 3 | —$CH_3$ |
| 38 | —$CH_3$ | —$CH_3$ | 1 | 3 | —$C_3H_7$ |
| 39 | —$CH_3$ | —$CH_3$ | 1 | 3 | —$C_3H_7$ |
| 40 | —$CH_3$ | —$CH_3$ | 1 | 3 | —$CH_2$—$C_6H_5$ |
| 41 | —$C_2H_5$ | H | 1 | 3 | H |
| 42 | —$C_2H_5$ | H | 1 | 3 | —$CH_3$ |
| 43 | —$C_2H_5$ | H | 1 | 3 | —$C_2H_5$ |
| 44 | —$C_2H_5$ | H | 1 | 3 | —$C_3H_7$ |
| 45 | —$C_2H_5$ | H | 1 | 3 | —$CH_2$—$C_6H_5$ |
| 46 | —$C_2H_5$ | —$C_2H_5$ | 1 | 3 | H |
| 47 | —$C_2H_5$ | —$C_2H_5$ | 1 | 3 | —$CH_3$ |
| 48 | —$C_2H_5$ | —$C_2H_5$ | 1 | 3 | —$C_2H_5$ |
| 49 | —$C_2H_5$ | —$C_2H_5$ | 1 | 3 | —$C_3H_7$ |
| 50 | —$C_2H_5$ | —$C_2H_5$ | 1 | 3 | —$CH_2$—$C_6H_5$ |
| 51 | n-$C_5H_{11}$ | H | 2 | 2 | H |
| 52 | n-$C_5H_{11}$ | H | 2 | 2 | —$CH_3$ |
| 53 | n-$C_5H_{11}$ | H | 2 | 2 | —$C_2H_5$ |
| 54 | n-$C_5H_{11}$ | H | 2 | 2 | —$C_3H_7$ |
| 55 | n-$C_5H_{11}$ | H | 2 | 2 | —$CH_2$—$C_6H_5$ |
| 56 | i-$C_5H_{11}$ | H | 2 | 2 | H |
| 57 | i-$C_5H_{11}$ | H | 2 | 2 | —$CH_3$ |
| 58 | i-$C_5H_{11}$ | H | 2 | 2 | —$C_2H_5$ |
| 59 | i-$C_5H_{11}$ | H | 2 | 2 | —$C_3H_7$ |
| 60 | i-$C_5H_{11}$ | H | 2 | 2 | —$CH_2$—$C_6H_5$ |
| 61 | $CH_2$=CH— | H | 2 | 2 | H |
| 62 | $CH_2$=CH— | H | 2 | 2 | —$CH_3$ |
| 63 | $CH_2$=CH— | H | 2 | 2 | —$C_2H_5$ |

TABLE 1-continued

| No. | $R^3$ | $R^4$ | m | n | R |
|---|---|---|---|---|---|
| 64 | $CH_2$=CH— | H | 2 | 2 | —$C_3H_7$ |
| 65 | $CH_2$=CH— | H | 2 | 2 | —$CH_2$—$C_6H_5$ |
| 66 | CH≡C— | H | 2 | 2 | H |
| 67 | CH≡C— | H | 2 | 2 | —$CH_3$ |
| 68 | CH≡C— | H | 2 | 2 | —$C_2H_5$ |
| 69 | CH≡C— | H | 2 | 2 | —$C_3H_7$ |
| 70 | CH≡C— | H | 2 | 2 | —$CH_2$—$C_6H_5$ |
| 71 | $(CH_3)_2N$—$CH_2CH_2$— | H | 2 | 2 | H |
| 72 | $(CH_3)_2N$—$CH_2CH_2$— | H | 2 | 2 | —$CH_3$ |
| 73 | $(CH_3)_2N$—$CH_2CH_2$— | H | 2 | 2 | —$C_2H_5$ |
| 74 | $(CH_3)_2N$—$CH_2CH_2$— | H | 2 | 2 | —$C_3H_7$ |
| 75 | $(CH_3)_2N$—$CH_2CH_2$— | H | 2 | 2 | —$CH_2$—$C_6H_5$ |
| 76 | $(CH_3)_2N$—$CH_2CH_2$— | $CH_3$— | 2 | 2 | H |
| 77 | $(CH_3)_2N$—$CH_2CH_2$— | $CH_3$— | 2 | 2 | —$CH_3$ |
| 78 | $(CH_3)_2N$—$CH_2CH_2$— | $CH_3$— | 2 | 2 | —$C_2H_5$ |
| 79 | $(CH_3)_2N$—$CH_2CH_2$— | $CH_3$— | 2 | 2 | —$C_3H_7$ |
| 80 | $(CH_3)_2N$—$CH_2CH_2$— | $CH_3$— | 2 | 2 | —$CH_2$—$C_6H_5$ |
| 81 | $(CH_3)_2N$—$CH_2CH_2$— | $C_3H_7$— | 2 | 2 | H |
| 82 | $(CH_3)_2N$—$CH_2CH_2$— | $C_3H_7$— | 2 | 2 | —$CH_3$ |
| 83 | $(CH_3)_2N$—$CH_2CH_2$— | $C_3H_7$— | 2 | 2 | —$C_2H_5$ |
| 84 | $(CH_3)_2N$—$CH_2CH_2$— | $C_3H_7$— | 2 | 2 | —$C_3H_7$ |
| 85 | $(CH_3)_2N$—$CH_2CH_2$— | $C_3H_7$— | 2 | 2 | —$CH_2$—$C_6H_5$ |
| 86 | $CF_3CH_2$— | $CF_3$— | 2 | 2 | H |
| 87 | $CF_3CH_2$— | $CF_3$— | 2 | 2 | —$CH_3$ |
| 88 | $CF_3CH_2$— | $CF_3$— | 2 | 2 | —$C_2H_5$ |
| 89 | $CF_3CH_2$— | $CF_3$— | 2 | 2 | —$C_3H_7$ |
| 90 | $CF_3CH_2$— | $CF_3$— | 2 | 2 | —$CH_2$—$C_6H_5$ |
| 91 | $CH_3CO$— | $CH_3CO$— | 2 | 2 | H |
| 92 | $CH_3CO$— | $CH_3CO$— | 2 | 2 | —$CH_3$ |
| 93 | $CH_3CO$— | $CH_3CO$— | 2 | 2 | —$C_2H_5$ |
| 94 | $CH_3CO$— | $CH_3CO$— | 2 | 2 | —$C_3H_7$ |
| 95 | $CH_3CO$— | $CH_3CO$— | 2 | 2 | —$CH_2$—$C_6H_5$ |
| 96 | $CH_3CH_2CH_2CO$— | $CH_3CO$— | 2 | 2 | H |
| 97 | $CH_3CH_2CH_2CO$— | $CH_3CO$— | 2 | 2 | —$CH_3$ |
| 98 | $CH_3CH_2CH_2CO$— | $CH_3CO$— | 2 | 2 | —$C_2H_5$ |
| 99 | $CH_3CH_2CH_2CO$— | $CH_3CO$— | 2 | 2 | —$C_3H_7$ |
| 100 | $CH_3CH_2CH_2CO$— | $CH_3CO$— | 2 | 2 | —$CH_2$—$C_6H_5$ |
| 101 | $HOOCCH_2$— | $CH_3$— | 2 | 2 | H |
| 102 | $HOOCCH_2$— | $CH_3$— | 2 | 2 | —$CH_3$ |
| 103 | $HOOCCH_2$— | $CH_3$— | 2 | 2 | —$C_2H_5$ |
| 104 | $HOOCCH_2$— | $CH_3$— | 2 | 2 | —$C_3H_7$ |
| 105 | $HOOCCH_2$— | $CH_3$— | 2 | 2 | —$CH_2$—$C_6H_5$ |
| 106 | F— | F— | 2 | 2 | H |
| 107 | F— | F— | 2 | 2 | —$CH_3$ |
| 108 | F— | F— | 2 | 2 | —$C_2H_5$ |
| 109 | F— | F— | 2 | 2 | —$C_3H_7$ |
| 110 | F— | F— | 2 | 2 | —$CH_2$—$C_6H_5$ |
| 111 | F— | F— | 1 | 3 | H |
| 112 | F— | F— | 1 | 3 | —$CH_3$ |
| 113 | F— | F— | 1 | 3 | —$C_2H_5$ |
| 114 | F— | F— | 1 | 3 | —$C_3H_7$ |
| 115 | F— | F— | 1 | 3 | —$CH_2$—$C_6H_5$ |
| 116 | Br— | Br— | 2 | 2 | H |
| 117 | Br— | Br— | 2 | 2 | —$CH_3$ |
| 118 | Br— | Br— | 2 | 2 | —$C_2H_5$ |
| 119 | Br— | Br— | 2 | 2 | —$C_3H_7$ |
| 120 | Br— | Br— | 2 | 2 | —$CH_2$—$C_6H_5$ |
| 121 | $CH_3(CH_2)_5$— | H | 2 | 2 | H |
| 122 | $CH_3(CH_2)_5$— | H | 2 | 2 | —$CH_3$ |
| 123 | $CH_3(CH_2)_5$— | H | 2 | 2 | —$C_2H_5$ |
| 124 | $CH_3(CH_2)_5$— | H | 2 | 2 | —$C_3H_7$ |
| 125 | $CH_3(CH_2)_5$— | H | 2 | 2 | —$CH_2$—$C_6H_5$ |
| 126 | $CF_3$— | $CF_3$— | 2 | 2 | H |
| 127 | $CF_3$— | $CF_3$— | 2 | 2 | —$CH_3$ |
| 128 | $CF_3$— | $CF_3$— | 2 | 2 | —$C_2H_5$ |
| 129 | $CF_3$— | $CF_3$— | 2 | 2 | —$C_3H_7$ |
| 130 | $CF_3$— | $CF_3$— | 2 | 2 | —$CH_2$—$C_6H_5$ |
| 131 | $CF_3$— | $CF_3$— | 1 | 3 | H |
| 132 | $CF_3$— | $CF_3$— | 1 | 3 | —$CH_3$ |
| 133 | $CF_3$— | $CF_3$— | 1 | 3 | —$C_2H_5$ |
| 134 | $CF_3$— | $CF_3$— | 1 | 3 | —$C_3H_7$ |
| 135 | $CF_3$— | $CF_3$— | 1 | 3 | —$CH_2$—$C_6H_5$ |

As the bisphosphonic acid derivative of the formula (I) wherein A is

the following compounds may, for example, be mentioned. In the following Table, Pip represents a piperidino group, Pyr represents a 2-pyridyl group, Bz represents a benzyl group, and Im represents a 4-imidazolyl group.

TABLE 2

| No. | $R^5$ | $R^6$ | | | R |
|---|---|---|---|---|---|
| 1 | Pip | H | 2 | 2 | H |
| 2 | Pip | H | 2 | 2 | $CH_3$— |
| 3 | Pip | H | 2 | 2 | $C_2H_5$— |
| 4 | Pip | H | 2 | 2 | $C_3H_7$— |
| 5 | Pip | H | 2 | 2 | Bz |
| 6 | $CH_3$— | $CH_3$— | 2 | 2 | H |
| 7 | $CH_3$— | $CH_3$— | 2 | 2 | $CH_3$— |
| 8 | $CH_3$— | $CH_3$— | 2 | 2 | $C_2H_5$— |
| 9 | $CH_3$— | $CH_3$— | 2 | 2 | $C_3H_7$— |
| 10 | $CH_3$— | $CH_3$— | 2 | 2 | Bz |
| 11 | Pyr | H | 2 | 2 | H |
| 12 | Pyr | H | 2 | 2 | $CH_3$— |
| 13 | Pyr | H | 2 | 2 | $C_2H_5$— |
| 14 | Pyr | H | 2 | 2 | $C_3H_7$— |
| 15 | Pyr | H | 2 | 2 | Bz |
| 16 | $C_2H_5$— | $C_2H_5$— | 2 | 2 | H |
| 17 | $C_2H_5$— | $C_2H_5$— | 2 | 2 | $CH_3$— |
| 18 | $C_2H_5$— | $C_2H_5$— | 2 | 2 | $C_2H_5$— |
| 19 | $C_2H_5$— | $C_2H_5$— | 2 | 2 | $C_3H_7$— |
| 20 | $C_2H_5$— | $C_2H_5$— | 2 | 2 | Bz |
| 21 | Ph | H | 2 | 2 | H |
| 22 | Ph | H | 2 | 2 | $CH_3$— |
| 23 | Ph | H | 2 | 2 | $C_2H_5$— |
| 24 | Ph | H | 2 | 2 | $C_3H_7$— |
| 25 | Ph | H | 2 | 2 | Bz |
| 26 | Ph | H | 1 | 3 | H |
| 27 | Ph | H | 1 | 3 | $CH_3$— |
| 28 | Ph | H | 1 | 3 | $C_2H_5$— |
| 29 | Ph | H | 1 | 3 | $C_3H_7$— |
| 30 | Ph | H | 1 | 3 | Bz |
| 31 | Bz | H | 2 | 2 | H |
| 32 | Bz | H | 2 | 2 | $CH_3$— |
| 33 | Bz | H | 2 | 2 | $C_2H_5$— |
| 34 | Bz | H | 2 | 2 | $C_3H_7$— |
| 35 | Bz | H | 2 | 2 | Bz |
| 36 | Bz | H | 1 | 3 | Bz |
| 37 | Bz | H | 1 | 3 | $CH_3$— |
| 38 | Bz | H | 1 | 3 | $C_2H_5$— |
| 39 | Bz | H | 1 | 3 | $C_3H_7$— |
| 40 | Bz | $NH_2CO$— | 1 | 3 | Bz |
| 41 | Pip | $NH_2CO$— | 2 | 2 | H |
| 42 | Pip | $NH_2CO$— | 2 | 2 | $CH_3$— |
| 43 | Pip | $NH_2CO$— | 2 | 2 | $C_2H_5$— |
| 44 | Pip | $NH_2CO$— | 2 | 2 | $C_3H_7$— |
| 45 | Pip | $NH_2CO$— | 2 | 2 | Bz |
| 46 | Pip | $NH_2CO$— | 1 | 3 | H |
| 47 | Pip | $NH_2CO$— | 1 | 3 | $CH_3$— |
| 48 | Pip | $NH_2CO$— | 1 | 3 | $C_2H_5$— |
| 48 | Pip | $NH_2CO$— | 1 | 3 | $C_2H_5$— |
| 49 | Pip | $NH_2CO$— | 1 | 3 | $C_3H_7$— |
| 50 | Pip | $NH_2CO$— | 1 | 3 | Bz |
| 51 | F | F | 2 | 2 | H |
| 52 | F | F | 2 | 2 | $CH_3$— |
| 53 | F | F | 2 | 2 | $C_2H_5$— |
| 54 | F | F | 2 | 2 | $C_3H_7$— |
| 55 | F | F | 2 | 2 | Bz |
| 56 | F | F | 1 | 3 | H |
| 57 | F | F | 1 | 3 | $CH_3$— |
| 58 | F | F | 1 | 3 | $C_2H_5$— |
| 59 | F | F | 1 | 3 | $C_3H_7$— |
| 60 | F | F | 1 | 3 | Bz |
| 61 | $CH_2=CH$— | H | 2 | 2 | H |
| 62 | $CH_2=CH$— | H | 2 | 2 | $CH_3$— |
| 63 | $CH_2=CH$— | H | 2 | 2 | $C_2H_5$— |
| 64 | $CH_2=CH$— | H | 2 | 2 | $C_3H_7$— |
| 65 | $CH_2=CH$— | H | 2 | 2 | Bz |
| 66 | $CH\equiv C$— | H | 2 | 2 | H |
| 67 | $CH\equiv C$— | H | 2 | 2 | $CH_3$— |
| 68 | $CH\equiv C$— | H | 2 | 2 | $C_2H_5$— |
| 69 | $CH\equiv C$— | H | 2 | 2 | $C_3H_7$— |
| 70 | $CH\equiv C$— | H | 2 | 2 | Bz |
| 71 | $(HOCH_2—)_2N$— | H | 2 | 2 | H |
| 72 | $(HOCH_2—)_2N$— | H | 2 | 2 | $CH_3$— |
| 73 | $(HOCH_2—)_2N$— | H | 2 | 2 | $C_2H_5$— |
| 74 | $(HOCH_2—)_2N$— | H | 2 | 2 | $C_3H_7$— |
| 75 | $(HOCH_2—)_2N$— | H | 2 | 2 | Bz |
| 76 | $(CH_3)_2N$— | $CH_3$— | 2 | 2 | H |
| 77 | $(CH_3)_2N$— | $CH_3$— | 2 | 2 | $CH_3$— |
| 78 | $(CH_3)_2N$— | $CH_3$— | 2 | 2 | $C_2H_5$— |
| 79 | $(CH_3)_2N$— | $CH_3$— | 2 | 2 | $C_3H_7$— |
| 80 | $(CH_3)_2N$— | $CH_3$— | 2 | 2 | Bz |
| 81 | $(CH_3)_2N$— | H | 2 | 2 | H |
| 82 | $(CH_3)_2N$— | H | 2 | 2 | $CH_3$— |
| 83 | $(CH_3)_2N$— | H | 2 | 2 | $C_2H_5$— |
| 84 | $(CH_3)_2N$— | H | 2 | 2 | $C_3H_7$— |
| 85 | $(CH_3)_2N$— | H | 2 | 2 | Bz |
| 86 | F | $CH_3$— | 2 | 2 | H |
| 87 | F | $CH_3$— | 2 | 2 | $CH_3$— |
| 88 | F | $CH_3$— | 2 | 2 | $C_2H_5$— |
| 89 | F | $CH_3$— | 2 | 2 | $C_3H_7$— |
| 90 | F | $CH_3$— | 2 | 2 | Bz |
| 91 | Cl | Cl | 2 | 2 | H |
| 92 | Cl | Cl | 2 | 2 | $CH_3$— |
| 93 | Cl | Cl | 2 | 2 | $C_2H_5$— |
| 94 | Cl | Cl | 2 | 2 | $C_3H_7$— |
| 95 | Cl | Cl | 2 | 2 | Bz |
| 96 | Cl | $CH_3$— | 2 | 2 | H |
| 97 | Cl | $CH_3$— | 2 | 2 | $CH_3$— |
| 98 | Cl | $CH_3$— | 2 | 2 | $C_2H_5$— |
| 99 | Cl | $CH_3$— | 2 | 2 | $C_3H_7$— |
| 100 | Cl | $CH_3$— | 2 | 2 | Bz |
| 101 | $CH_3$— | HO— | 2 | 2 | H |
| 102 | $CH_3$— | HO— | 2 | 2 | $CH_3$— |
| 103 | $CH_3$— | HO— | 2 | 2 | $C_2H_5$— |
| 104 | $CH_3$— | HO— | 2 | 2 | $C_3H_7$— |
| 105 | $CH_3$— | HO— | 2 | 2 | Bz |
| 106 | $CH_3(CH_2)_5$— | HO— | 2 | 2 | H |
| 107 | $CH_3(CH_2)_5$— | HO— | 2 | 2 | $CH_3$— |
| 108 | $CH_3(CH_2)_5$— | HO— | 2 | 2 | $C_2H_5$— |
| 109 | $CH_3(CH_2)_5$— | HO— | 2 | 2 | $C_3H_7$— |
| 110 | $CH_3(CH_2)_5$— | HO— | 2 | 2 | Bz |
| 111 | $C_2H_5$— | HO— | 2 | 2 | H |
| 112 | $C_2H_5$— | HO— | 2 | 2 | $CH_3$— |
| 113 | $C_2H_5$— | HO— | 2 | 2 | $C_2H_5$— |
| 114 | $C_2H_5$— | HO— | 2 | 2 | $C_3H_7$— |
| 115 | $C_2H_5$— | HO— | 2 | 2 | Bz |
| 116 | 4-F-Ph | H | 2 | 2 | H |
| 117 | 4-F-Ph | H | 2 | 2 | $CH_3$— |
| 118 | 4-F-Ph | H | 2 | 2 | $C_2H_5$— |
| 119 | 4-F-Ph | H | 2 | 2 | $C_3H_7$— |
| 120 | 4-F-Ph | H | 2 | 2 | Bz |
| 121 | 4-$CH_3$—Ph | H | 2 | 2 | H |
| 122 | 4-$CH_3$—Ph | H | 2 | 2 | $CH_3$— |
| 123 | 4-$CH_3$—Ph | H | 2 | 2 | $C_2H_5$— |
| 124 | 4-$CH_3$—Ph | H | 2 | 2 | $C_3H_7$— |
| 125 | 4-$CH_3$—Ph | H | 2 | 2 | Bz |
| 126 | Im | H | 2 | 2 | H |
| 127 | Im | H | 2 | 2 | $CH_3$— |
| 128 | Im | H | 2 | 2 | $C_2H_5$— |
| 129 | Im | H | 2 | 2 | $C_3H_7$— |
| 130 | Im | H | 2 | 2 | Bz |
| 131 | n-$C_3H_7$— | HO— | 2 | 2 | H |
| 132 | n-$C_3H_7$— | HO— | 2 | 2 | $CH_3$— |
| 133 | n-$C_3H_7$— | HO— | 2 | 2 | $C_2H_5$— |
| 134 | n-$C_3H_7$— | HO— | 2 | 2 | $C_3H_7$— |
| 135 | n-$C_3H_7$— | HO— | 2 | 2 | Bz |
| 136 | i-$C_3H_7$— | HO— | 2 | 2 | H |
| 137 | i-$C_3H_7$— | HO— | 2 | 2 | $CH_3$— |
| 138 | i-$C_3H_7$— | HO— | 2 | 2 | $C_2H_5$— |
| 139 | i-$C_3H_7$— | HO— | 2 | 2 | $C_3H_7$— |
| 140 | i-$C_3H_7$— | HO— | 2 | 2 | Bz |
| 141 | t-$C_4H_9$— | HO— | 2 | 2 | H |
| 142 | t-$C_4H_9$— | HO— | 2 | 2 | $CH_3$— |
| 143 | t-$C_4H_9$— | HO— | 2 | 2 | $C_2H_5$— |
| 144 | t-$C_4H_9$— | HO— | 2 | 2 | $C_3H_7$— |
| 145 | t-$C_4H_9$— | HO— | 2 | 2 | Bz |
| 146 | n-$C_4H_9$— | HO— | 2 | 2 | H |
| 147 | n-$C_4H_9$— | HO— | 2 | 2 | $CH_3$— |

TABLE 2-continued

| No. | $R^5$ | $R^6$ | | | R |
|---|---|---|---|---|---|
| 148 | n-C$_4$H$_9$— | HO— | 2 | 2 | C$_2$H$_5$— |
| 149 | n-C$_4$H$_9$— | HO— | 2 | 2 | C$_3$H$_7$— |
| 150 | n-C$_4$H$_9$— | HO— | 2 | 2 | Bz |

Now, the present invention will be described in further detail with reference to examples. However, it should be understood that the present invention is by no means restricted by such specific examples.

EXAMPLE 1

Preparation of tetraethyl-3-azaspiro[5.5]undecan-3-y-methylene bisphosphonate

A mixture comprising 10 g (58 mmol) of 3-azaspiro[5.5]undecane, 25 g (181 mmol) of diethyl phosphite and 10.3 g (70 mmol) of HC (OC$_2$H$_5$)$_3$, was stirred at 140° C. for 15 hours. To the reaction solution, 300 ml of chloroform was added, and the mixture was washed twice with 100 ml of a 2N sodium hydroxide aqueous solution. The chloroform solution was washed with water and dried. Then, chloroform was distilled off under reduced pressure to give 40 g of a slightly yellow oily substance. This oily substance was purified by silica gel column chromatography to give 20 g of the above identified compound as an oily substance.

Rf value: 0.57 (silicagel plate, chloroform/methanol = 10/1).

$^1$H-NMR(CDCl$_3$) δ value, 1.33(2H,t,CH$_3$×4), 1.34–1.45(14H,m,ringCH$_2$×7), 2.91–2.99(4H,m,C-H$_2$—N—CH$_2$), 1.36(1H,dd,CH), 4.10–4.28(8H,m,CH$_2$CH$_3$×4).

MS(EI): 439(M+), 302.

EXAMPLE 2

Preparation of 3-azaspiro[5.5]undecan-3-yl-methylene bisphosphonic acid

A mixture comprising 17.6 g (40 mmol) of tetraethyl-3-azaspiro[5.5]undecan-3-yl-methylene bisphosphonate obtained in Example 1 and 140 ml of 6N hydrochloric acid was stirred at a temperature of from 95° to 100° C. for 96 hours. The reaction solution was subjected to distillation under reduced pressure to distill hydrochloric acid off to give an oily substance. To this oily substance, water was added, and then water was distilled under reduced pressure from the aqueous solution. This operation was repeated, and when colorless crystalline powder started to precipitate, the distillation was stopped. Then, a small amount of ethanol was added to the aqueous solution. Crystalline powder gradually precipitated, and it was collected by filtration. The crystalline powder was washed with ethanol and ethyl ether and dried to give 7 g of the above identified compound.

mp: 232°–234° C.

$^1$H-NMR(D$_2$O): δ value, 1.25–1.65(12H,m,ringCH$_2$×6), 1.83–2.0(2H,m,ringCH$_2$), 3.17(1H,dd,CH), 3.32–3.48(2H,m,NCH$_2$), 3.76–3.98(3H,m,NCH$_2$).

MS(FAB): [M-H]−326.

In the above operation, when the colorless crystalline powder started to precipitate, the distillation was further continued for concentration and drying to give crystalline powder, which was washed with ethyl ether and ethanol and dried to give the above identified compound, which showed a melting point of from 222° to 225° C. $^1$H-NMR and MS(FAB) thereof were the same as above.

EXAMPLE 3

Preparation of tetraethyl-1,1-difluoro-6-azaspiro[2.5]octan-6-yl-methylene bisphosphonate 10.5 g of 4-methylidene-N-benzylpiperidine was dissolved in 100 ml of tetrahydrofuran (THF), and 15 ml of CBr$_2$F$_2$ was added in the presence of 150 ml of diethylzinc. The mixture was reacted at room temperature for 10 hours to give 6.0 g of 1,1-difluoro-6-aza-N-benzylspiro[2.5]octane. Then, 6.0 g of this substance was mildly heated together with 1-chloroethyl chloroformate and further heated with 50 ml of methanol. Then, the solvent was distilled off to give 3.2 g (yield: 88%) of 1,1-difluoro-6-azaspiro[2.5]octane.

Then, 3.2 g of this substance was treated in the same manner as in Example 1 to give 7.2 g (yield: 77%) of the above identified compound. Rf value: 0.63 (silicagel plate, chloroform/methanol = (10/1)).

$^1$H-NMR(CDCl$_3$): δ value, 1.32–1.40(6H,m,CH$_3$×2), 1.71–1.77(4H,m,4–8-CH$_2$), 2.75(2H,t,J=17Hz,2-CH$_2$), 2.85–2.96(2H,m,5- or 7-CH$_2$), 3.26–3.30(2H,m,5- or 7-CH$_2$), 3.36(1H,t,J=25Hz,NCH), 4.13–4.26(4H,m,CH$_3$CH$_2$×2).

MS(EI): 433(M+).

EXAMPLE 4

Preparation of 1,1-difluoro-6-azaspiro[2.5]octan-6-yl-methylene bisphosphonic acid 0.86 g (1.5 mmol) of tetraethyl-1,1-difluoro-6-azaspiro[2.5]octan-6-yl-methylene bisphosphonate obtained in Example 3, was reacted in the same manner as in Example 2 to give a colorless powder, which was recrystallized from ethanol/ethyl acetate (1/1) to give 260 mg of the above identified compound as colorless prism crystals (yield: 54%).

mp: 231°–233° C. (decomposed).

$^1$H-NMR(D$_2$O): δ value, 2.08–2.16(4H,m,4-,8-CH$_2$), 2.94(2H,t,J=16Hz, 2-CH$_2$), 3.45–3.55(2H,m,5- or 7-CH$_2$), 3.65(1H,t,J=18Hz,NCH), 4.03–4.17(2H,m,5- or 7-CH$_2$).

MS(FAB): [M-H]−320

EXAMPLE 5

Preparation of tetraethyl-8-azaspiro[4.5]decan-8-yl-methylene bisphosphonate

To 50 g of 3,3-tetramethylene glutaric anhydride, 32.5 ml of benzylamine was added, and the mixture was reacted at 220° C. to give 55.4 g (yield: 73%) of a crystalline benzylimide product. Then, 55 g of this benzylimide product was reacted with lithium aluminum hydride (LiAlH$_4$) in THF to give 35.6 g (yield: 73%) of N-benzyl-4,4-tetramethylpiperidine. To a dichloroethane solution (700 ml) containing 35.6 g of this N-benzyl product, 18.4 ml of a-chloroethyl chloroformate was dropwise added, and the mixture was refluxed under heating and then added to methanol. The mixture was further refluxed under heating to give 25 g (yield: 22%) of 8-azaspiro[4.5]decane.

$^1$H-NMR(CDCl$_3$): δ value, 1.34–1.72(12H,m,1-,2-,3-,4-,6-,10-CH$_2$), 2.83–2.94(4Hrm,7-,9-CH$_2$), 5.20(1H,br s,NH).

MS(EI): 228(M+-1), 152.

2.6 g of this 8-azaspiro[4.5]decane was treated in the same manner as in Example 1 to give 3.4 g (yield: 43%) of the above identified compound.

Rf value: 0.63 (silicagel plate, chloroform/methanol (50/1)).

$^1$H-NMR(CDCl$_3$): δ value, 1.31–1.43(12H,m,CH$_3$×4), 1.35–1.48(8H,m,1-,2-,3-,4-,CH$_2$), 1.55–1.63(4H,m,6-,10-CH$_2$), 2.92–3.00(4H,m,7-,9-CH$_2$), 3.36(1H,t,J=25Hz,NCH), 4.23–4.30(8H,m,CH$_3$$\underline{CH_2}$×4).

MS(EI): 425(M+), 288.

EXAMPLE 6

Preparation of 8-azaspiro[4.5]decan-8-yl-methylene bisphosphonic acid 1 g of tetraethyl-8-azaspiro[4.5]decan-8-yl-methylene bisphosphonate obtained in Example 5 was heated in the same manner as in Example 2 to give 0.46 g (yield: 63%) of the above identified compound as colorless prism crystals.

mp: 177°–181° C. (decomposed).

$^1$H-NMR(CDCl$_3$): δ value, 1.39–1.69(8H,m,1-,2-,3-,4-CH$_2$), 1.68–1.86(4H,m,6-,10-CH$_2$), 3.15(1H,t,J=18Hz,NCH), 3.35–3.65(2H,m,7- or 9-CH$_2$), 3.65–3.98(2H,m,7- or 9-CH$_2$).

MS(FAB): [M-H]$^-$312.

EXAMPLE 7

Preparation of tetraethyl-1-azaspiro[4-5]decan-1-yl-methylene bisphosphonate 99.5 g of nitrocyclohexane was dissolved in 40 ml of t-butanol, and 83.4 ml of ethyl acrylate was added thereto in the presence of 7 ml of 40% Triton B. The mixture was reacted at room temperature to give 153 g (yield: 87%) of 1-nitro-1-(2-ethoxycarbonylethyl)cyclohexane. Then, 20 g of this substance was dissolved in ethanol and 3.6 g of Raney nickel was added thereto. The mixture was strongly stirred in the presence of hydrogen gas (70 kg/cm$^2$), and then the Raney nickel was removed. The reaction solution was refluxed under heating for 5 hours. Then, ethanol was distilled off to give 8.0 g (yield: 62%) of 1-aza-2-oxospiro[4.5-]decane8.0 g of this substance was dissolved in 30 ml of THF, and 3.6 g of LiAlH$_4$ was added thereto. The mixture was reacted at room temperature for 15 hours to give 7.4 g (yield: 83%) of 1-azaspiro[4.5]decane.

$^1$H-NMR(CDCl$_3$): δ value, 1.27–1.81(14H,m,3-,4-,6-,7-,8-,9-,10-CH$_2$), 2.93(2H,t,J=7Hz,2-CH$_2$).

MS(EI): 139(M++1), 96.

5.6 g of this 1-azaspiro[4.5]decane was treated in the same manner as in Example 1 to give 12.8 g (yield: 75%) of the above identified compound as an oily substance.

Rf value: 0.72 (silicagel plate, chloroform/methanol (20/1)).

$^1$H-NMR(CDCl$_3$): δ value, 1.18–1.78(14H,m,3-,4-,6,7-,8-,9-,10-CH$_2$), 1.28–1.39(12H,m,CH$_3$×4), 3.29–3.38(2H,m,2-CH$_2$), 3.81(1H,t,J=25Hz,NCH),4.10–4.26(8H,m,CH$_3$$\underline{CH_2}$×4).

MS(EI): 425(M+), 381, 287.

EXAMPLE 8

Preparation of 1-azaspiro[4.5]decan-1-yl-methylene bisphosphonic acid 1 g (2.4 mmol) of tetraethyl-1-azaspiro[4.5]decan-1-yl-methylene bisphosphonate obtained in Example 7 was dissolved in 30 ml of dry carbon tetrachloride (CCl$_4$) and 2.3 g (11.5 mmol) of methylsilyl iodide was added thereto at 0° C. under an argon stream. This reaction solution was stirred for 30 minutes at 0° C. Then, the solvent was distilled off under reduced pressure, and 150 ml of water was added to the residue. The mixture was washed with ethyl ether. The aqueous layer was concentrated under reduced pressure, and isopropanol/isopropyl ether (1/1) was added to the residue, and the mixture was left to stand to give 0.49 g (yield: 65%) of the above identified compound as colorless crystals.

mp: at least 290° C. (as disodium salt).

$^1$H-NMR(D$_2$O): δ value, 1.13–2.16(14H,m,3-,4-,6-,7-,8-,9-,10-CH$_2$), 3.53(1H,t,J=17Hz,NCH), 3.70–3.87(2H,m,2-CH$_2$) (as disodium salt).

MS(FAB): 312[M-H]$^-$.

EXAMPLE 9

Preparation of tetraethyl-1-azaspiro[5.5]undecan-1-yl-methylene bisphosphonate 30 g of 1-nitro-1-( 2-ethoxycarbonylethyl)cyclohexane obtained in the same manner as in Example 7 was heated together with 300 ml of a 3N sodium hydroxide aqueous solution to give 23 g of 1-nitro-1-(2-carboxyethyl)cyclohexane. This product was added to 200 ml of thionyl chloride (SOCl$_2$), and the mixture was heated to give 21 g of 1-nitro-1-(2-chlorocarbonylethyl)cyclohexane. 20 g of this substance was dissolved in 60 ml of ethyl ether, and 14.5 g of diazomethane (CH$_2$N$_2$) (as a 15% ethyl ether solution) was added thereto at room temperature. Under completion of the reaction, the solvent was distilled off. To the residue, 10 g of silver oxide (Ag$_2$O) and 100 ml of ethanol were added, and the mixture was refluxed under heating for 3 hours to give 6.5 g (yield: 27%) of 1-nitro-1-(3-ethoxycarbonylpropyl)cyclohexane.

6.5 g of this substance was stirred with hydrogen gas (65 kg/cm$^2$) in 100 ml of ethanol in the presence of 3.5 g of Raney nickel. The Raney nickel was removed from the reaction solution. Then, the reaction solution was refluxed under heating to give 1.7 g (yield: 39%) of 1-aza-2-oxospiro[5.5]undecane. 1.7 g of this substance was dissolved in 50 ml of THF and reacted with 1.1 g of LiAlH$_4$ to give 1.0 g of 1-azaspiro[5.5]undecane.

$^1$H-NMR(CDCl$_3$): δ value, 1.31–1.58(16H,m,3-,4-,5-,7-,8-,9-,10-,11-CH$_2$), 2.74–2.83(2H,m,2-CH$_2$), 3.31(1H,br s,NH).

MS(EI): 153(M+), 110, 1.0 g of this 1-azaspiro[5.5]undecane was treated in the same manner as in Example 2 to give 1.3 g (yield: 45%) of the above identified compound as an oily substance.

Rf value: 0.71 (silicagel plate, chloroform/methanol (10/1)).

$^1$H-NMR(CDCl$_3$): δ value, 1.28–1.36(12H,m,CH$_3$×4), 1.20–182(16H,m,3-,4-,5-,7-,8-,9-,10-,11-CH$_2$), 3.21–3.27(2H,m,2-CH$_2$), 4.10(1H,t,J=26Hz,NCH), 4.09–4.27 (8H,m,CH$_3$$\underline{CH_2}$×4).

MS(EI): $\overline{439}$(M+).

EXAMPLE 10

Preparation of 1-azaspiro[5.5]undecan-1-yl-methylene - bisphosphonic acid 0.74 g (2.2 mmol) of tetraethyl-1-azaspiro[5.5]undecan-1-yl-methylene bisphosphonate obtained in Example 9 was dissolved in 10 ml of a 25% hydrogen bromide (HBr) acetic acid solution at 0° C., and the temperature was slowly raised. The solution was stirred at 60° C. for further one hour. The reaction solution was concentrated under reduced pressure, and 0.73 g of the residue was purified by developing with methanol by means of Lobar column (RP-8, size B), (manufactured Merck Co.) to give 260 mg (yield: 36%) of the above identified compound as colorless powdery crystals.

mp: 240°–245° C. (decomposed).

$^1$H-NMR(D$_2$O): δ value, 1.13–2.19(16H,m,3-,4-,5-,7-,8-,9-, 10-,11-CH$_2$), 3.62–3.85(2H,m,2-CH$_2$), 3.70(1H,t,J=19Hz,NCH) (as disodium salt).

MB(FAB): 372[M+H]$^+$.

EXAMPLE 11

Preparation of tetraethyl-2-azaspiro[5.5]undecan-2-yl-methylene bisphosphonate

Cyclohexanealdehyde and acrylonitrile were dissolved in t-butanol, and a 30% potassium hydroxide-ethanol solution was added to give 1-formyl-1-(3-cyanoethyl)cyclohexane. This formyl product was reacted with ethylene glycol in benzene in the presence of tosyl acid to give an acetal product. To a THF solution of the acetal product, LiAlH$_4$ was added for reduction, followed by treatment with an aqueous hydrochloric acid solution to give 2-azaspiro[5.5]undecan-1,2-ene. This imine product was stirred with hydrogen gas (5 kg/cm$^2$) in methanol in the presence of 10% Pd-C to give 2azaspiro[5.5]undecane.

$^1$H-NMR(CDCl$_3$): δ value, 1.11–1.63(14H,m,4-,5-,7-,8-9-,10-,11-CH$_2$), 2.57(2H,s,1-CH$_2$), 3.23(1H,br s,NH).

MS(EI): 153(M+), 110.

1.5 g of this 2-azaspiro[5.5]undecane was treated in the same manner as in Example 1 to give 4.1 g (yield: 72%) of the above identified compound as an oily substance.

Rf value: 0.63 (silicagel plate, chloroform/methanol (10/1)).

$^1$H-NMR(CDCl$_3$): δ value, 1.27–1.38(12H,m,CH$_3$×4), 1.22–1.60(14H,m,4-,5-,7-,8-,9-,10-,11-CH$_2$), 2.75(2H,s,1-CH$_2$), 2.98–2.96(2H,m,3-CH$_2$), 3.32(1H,t,J=25Hz,NCH), 4.13–4.26(8H,m,CH$_3$CH$_2$×4).

MS(EI): 439(M+).

EXAMPLE 12

Preparation of 2-azaspiro[5.5]undecan-2-yl-methylene bisphosphonic acid 1.5 g of tetraethyl-2-azaspiro[5.5]undecan-2-yl-methylene bisphosphonate obtained in Example 11 was treated in the same manner as in Example 2 to give 0.58 g (yield: 53%) of the above identified compound as colorless powdery crystals.

mp: 240°–245° C. (decomposed).

$^1$H-NMR(D$_2$O): δ value, 1.11–198(14H,m,4-,5-,7-,8-,9-,10-,11-CH$_2$), 3.17(1H,t,J=18Hz,NCH), 3.38(2H,s,1-CH$_2$), 3.46–3.65(2H,m,3-CH$_2$).

MS(FAB): 376[M-H]$^-$.

EXAMPLE 13

Preparation of 4-methylidenepiperidinomethylene bisphosphonic acid ethyl ester [R$^3$=R$^4$=H, R=13C$_2$H$_5$, m=n=2)

A mixture comprising 13.7 g (100 mmol) of 4-methylidenepiperidine hydrochloride, 20.2 g (200 mmol) of triethylamine, 35.6 g (240-mmol) of HC(OC$_2$H$_5$)$_3$ and 85.6 (620 mmol) of diethyl phosphite, was stirred at 140° C. for 6 hours. To the reaction solution, 250 ml of ethyl ether was added, and the mixture was washed with 100 ml of a 0.5N sodium hydroxide aqueous solution and 500 ml of water, and then concentrated under reduced pressure. The residue was distilled under reduced pressure to give 23 g (yield: 58%) of the above identified compound.

bp: 180°–185° C. (1.5 mmHg).

$^1$H-NMR(CDCl$_3$)δ value: 1.35(12H,t,CH$_3$×4), 2.20–2.24[4H,m, —C$\underline{H}_2$(CH$_2$=)CC$\underline{H}_2$-], 2.99–3.03(4H,m,

—CH$_2$NCH$_2$—), 3.41(1H,t,—NCH—), 4.14–4.29(8H,m,CH$_3$CH$_2$-×4), 4.65(2H,s,CH$_2$=).

MS(EI): 383(M+), 246.

EXAMPLE 14

Preparation of 4-methylidenepiperidinomethylene bisphosphonic acid (R$^3$=R$^4$=R=H,m=n=2)

23 g (59.9 mmol) of 4-methylidenepiperidinomethylene bisphosphonic acid ethyl ester obtained in Example 13 was added to 200 ml of dried CHCl$_3$, and the mixture was cooled to 0° C. Then, 49.1 g (245.6 mmol) of Me$_3$SiI was added thereto. This reaction solution was stirred at 0° C. for one hour. Then, the solvent was distilled off under reduced pressure. To the residue, methanol was added to give colorless crude crystals. The crude crystals were recrystallized from methanol/water to give 13.9 g (yield: 86%) of the above identified compound as colorless plate crystals.

mp: 231.5°–233.0° C.

$^1$H-NMR(D$_2$O) δ value: 2.54–2.59[4H,-m,—CH$_2$(CH$_2$=)CCH$_2$—], 3.21(1H,t, —NCH—), 3.67–3.72(4H,m,

—CH$_2$NCH$_2$—), 4.94(2H,s,—CH$_2$=) (as sodium salt).

MS(FAB): 270 [M-H]$^-$.

EXAMPLE 15

Preparation of 4-hexylidenepiperidinomethylene bisphosphonic acid ethyl ester (R$^3$=CH$_3$(CH$_2$)$_4$—, R$^4$=H, R=—C$_2$H$_5$, m=n=2)

A mixture comprising 6.0 g (28.8 mmol) of 4-hexylidenepiperidine hydrochloride, 6.6 g(65.4 mmol) of Et$_3$N, 10.8 g (72.9 mmol) of CH(OEt)$_3$ and 25.8 g (186.9 mmol) of diethyl phosphite, was stirred at 140° C. for 10 hours. To the reaction solution, 450 ml of chloroform was added, and the mixture was washed with 300 ml of a 0.5N sodium hydroxide aqueous solution and 1500 ml of water. Then, the solvent was distilled off under reduced pressure, and the residue thereby obtained was purified by silica gel column chromatography to give 9.3 g (yield: 71%) of the above identified compound as an oily substance.

Rf value: 0.71 (silicagel plate, ethanol/benzene/chloroform (1/90/90)).

$^1$H-NMR(CDCl$_3$)$\delta$ value: 0.88(3H,t,—CH$_2$CH$_2$C$\underline{H}_3$), 1.35(12H,t,—OCH$_2$C$\underline{H}_3\times 4$), 1.25–1.35(6H,m,—CH$_2$C$\underline{H}_2$C$\underline{H}_2$CH$_2$CH$_3$), 1.92–2.13(2H,m,=CHC$\underline{H}_2$—), 2.15–2.24[4H,m,—CH$_2$(=C)CH$_2$—], 2.95–2.98(4H,m,

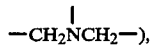
—CH$_2$NCH$_2$—), 3.40(1H,t,NCH—), 4.14–4.29(8H,m,—OC$\underline{H}_2$CH$_3\times 4$), 5.12(1H,t,HC=).
MS(EI): 453(M+), 316.

EXAMPLE 16

Preparation of 4-hexylidenepiperidinomethylene bisphosphonic acid (R$^3$=CH$_3$(CH$_2$)$_4$—, R$^4$=R=H, m=n=2)

9 g (20 mmol) of 4-hexylidenepiperidinomethylene bisphosphonic acid ethyl ester obtained in Example 15 was added to 70 ml of dried CCl$_4$, and the mixture was cooled to 2° C. Then, 16.4 g (82 mmol) of Me$_3$SiI was added thereto. This reaction solution was stirred at 2° C for one hour. Then, the solvent was distilled off under reduced pressure. To the residue, methanol was added, followed by recrystallization to give 6.6 g (yield: 97%) of the above identified compound as colorless flaky crystals.

mp: 223.5°–225.0° C.

$^1$H-NMR(D$_2$O)$\delta$ value: 0.87(3H,t,—CH$_2$CH$_2$C$\underline{H}_3$), 1.29–1.39(6H,m, —CH$_2$CH$_2$CH$_2$C$\underline{H}_3$), 2.03–2.06(2H,m, =CHC$\underline{H}_2$—), 2.50–2.75(4H,m,

—CH$_2$NCH$_2$—), 3.30(1H,t,—NCH—), 3.60–3.72(4H,m,

—CH$_2$NCH$_2$—), 5.45(1H,t,=CH—) (as sodium salt).
MS(EI): Not detected.

EXAMPLE 17

Preparation of 4-ethylidenepiperidinomethylene bisphosphonic acid ethyl ester (R$^3$=—CH$_3$, R$^4$=H, R=—C$_2$H$_5$, m=n=2)

To a THF (50 ml) solution of 7.5 (20 mmol) of ethyl triphenylphosphonium bromide, 2.5 ml (20 mmol) of a 1.6M BuLi hexane solution was added under cooling with ice. Then, 5.8 g (15 mmol) of 4-oxopiperidinomethylene bisphosphonic acid ethyl ester was dropwise added thereto. The mixture was stirred at room temperature for 24 hours. Then, 100 ml of hexane was added to the reaction solution, and the mixture was washed with water and dried. Then, the solvent was distilled off to give an oily residue. This residue was purified by silica gel column chromatography to give 3.5 g (yield: 58.7%) of the above identified compound Rf value: 0.87 (silicagel plate, chloroform/methanol (9/1)).

$^1$H-NMR(CDCl$_3$)$\delta$ value: 1.35(12H,t,—OCH$_2$C$\underline{H}_3\times 4$), 1.56(3H,d,=CHC$\underline{H}_3$), 2.13–2.25 [4H,m,—C$\underline{H}_2$(=C)CH$_2$—], 2.95–3.00(4H,m,

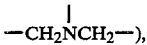
—CH$_2$NCH$_2$—), 3.41(1H,t,—NCH—), 4.15–4.30(8H,m, —OC$\underline{H}_2$CH$_3\times 4$), 5.18(1H,q,HC=).
MS(EI): 397(M+), 260.

EXAMPLE 18

Preparation of 4-ethylidenepiperidinomethylene bisphosphonic acid (R$^3$=—CH$_3$, R$^4$=R=H, m=n=2)

To a CCl$_4$ (10 ml) solution containing 0.9 g (2.2 mmol) of 4-ethylidenepiperidinomethylene bisphosphonic acid ethyl ester obtained in Example 17, 1.8 g (9.0 mmol) of Me$_3$SiI was added at 0° C., and the mixture was stirred at room temperature for one hour. Then, the reaction solution was concentrated under reduced pressure. The residue was recrystallized from methanol to give 0.55 g (yield: 88.2%) of the above identified compound.

mp: 228.0°–229.5° C.

$^1$H-NMR(D$_2$O)$\delta$ value: 1.62(3H,d,CH$_3$CH=), 2.43–2.71[4H,m,—CH$_2$(=C)CH$_2$—], 3.30(1H,t,—NCH—), 3.59–3.71(4H,m,

—CH$_2$NCH$_2$—), 5.49(1H,q,CH$_3$C$\underline{H}$=) (as sodium salt).
MS(EI): Not detected.

EXAMPLE 19

4-Propylidenepiperidinomethylene bisphosphonic acid ethyl ester (R$^3$=R=—C$_2$H$_5$, R$^4$=H, m=n=2)

Rf value: 0.67 ( silicagel plate, chloroform/methanol (20/1 )).

$^1$H-NMR(CDCl$_3$)$\delta$ value: 0.98(3H,t,J=8Hz,CH$_3$CH$_2$CH), 1.32–1.38(12H,m,C$\underline{H}_3$CH$_2$O$\times$4), 1.92–2.04(2H,m,C$\underline{H}_3$CH$_2$CH=), 2.12–2.20(4H,m,2-,6-CH$_2$), 2.93–3.02(4H,m,3-,5-CH$_2$), 3.41(1H,t,J=25Hz,NCH), 4.16–4.27(8H,m,CH$_3$C$\underline{H}_2$O$\times$4), 5.13(1H,t,J=6Hz,CH$_3$CH$_2$C$\underline{H}$=).
MS: 411(M+).

EXAMPLE 20

4-Propylidenepiperidinomethylene bisphosphonic acid ethyl ester (R$^3$=—C$_2$H$_5$, R$^4$=R=H, m=n=2)

mp: 235°–237° C.

$^1$H-NMR(D$_2$O): 0.88–0.99(3H,m,CH$_3$), 1.96–2.12(2H,m,CH$_3$C$\underline{H}_2$), 2.42–2.66(4H,m,3-,5-CH$_2$), 3.15(1H,t,J=15Hz,NC$\underline{H}$), 3.56–3.71(4H,m,2-,6-CH$_2$), 5.44(1H,m,=CH).
MS(FAB): 298[M-H]$^-$.

EXAMPLE 21

4-Butylidenepiperidinomethylene bisphosphonic acid ethyl ester ($R^3$=—$C_2H_7$, $R^4$=H, R=—$C_2H_5$, m=n=2)

Rf value: 0.51 (silicagel plate, chloroform/methanol (10/1)).

$^1$H-NMR(CDCl$_3$): 0.88(3H,t,J=7Hz,CH$_3$CH$_2$), 1.26–1.39(2H,m,CH$_3$CH$_2$), 1.90–2.00(2H,m,CH$_2$CH=), 2.12–2.26(2H,m,3-,5-CH$_2$), 2.94–3.02(4H,m,2-,6-CH$_2$), 3.40(1H,t,J=25Hz,NCH), 4.14–4.28(8H,m,CH$_3$C-H$_2$O×4), 5.12(1Ht,J=7Hz,CH=).

MS: 425(M+).

EXAMPLE 22

4-Butylidenepiperidinomethylene bisphosphonic acid ($R^3$=—$C_3H_7$, $R^4$=R=H, m=n=2)

mp: 226°–228° C.

$^1$H-NMR(D$_2$O): 0.81–0.92(3H,m,CH$_3$),1.-32–1.44(2H,m,CH$_3$CH$_2$), 1.97–2.07(2H,m,CH$_2$CH=), 2.44–2.67(4H,m,3-,5-CH$_2$), 3.33(1H,t,J=17Hz,NCH), 3.60–3.69(4H,m,2-,6-CH$_2$), 5.46(1H,t,J=7Hz,CH=).

MS(FAB): 312[M-H]−.

EXAMPLE 23

3-Methylidenepiperidinomethylene bisphosphonic acid ethyl ester ($R^3$=$R^4$H, R=—$C_2H_5$, m=1, n=3)

Rf value: 0.67 (silicagel plate, chloroform/methanol (9/1)).

$^1$H-NMR(CDCl$_3$): 1.29–1.38(12H,m,CH$_3$×4), 1.57–1.66(2H,m,5-CH$_2$), 2.08–2.15(2H,m,4-CH$_2$), 3.04–3.10(2H,m,6-CH$_2$), 3.37(1H,t,J=25Hz,NCH), 3.47–3.49(2H,m,2-CH$_2$), 4.13–4.27(8H,m,CH$_3$CH$_2$×4), 4.66(1H,br s, one of CH$_2$=), 4.72(1H,br s, one of CH$_2$=).

MS: 388(M+).

EXAMPLE 24

3-Methylidenepiperidinomethylene bisphosphonic acid ($R^3$=$R^4$=RH, m=1, n=3)

mp: 237°–239° C.

$^1$H-NMR(D$_2$O):
1.71–2.53(4H,m,4-,5-CH$_2$), 3.67(1H,t,J=25Hz,NCH), 3.74–3.85(2H,m,6-CH$_2$), 4.03(1H,d,J=13Hz, one of 2CH$_2$), 4.37(1H,d,J=13Hz, one of 2-CH$_2$), 5.15(2H,br s,CH2=).

EXAMPLE 25

4-Phenylpiperidinomethylene bisphosphonic acid ethyl ester

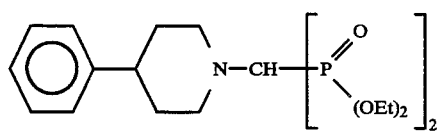

A mixture comprising 5 g (30 mmol) of phenylpiperidine, 5.3 g (36 mmol) of HC(OEt)$_3$ and 12.8 g (93 mmol) of (EtO)$_2$PHO, was stirred at 140° C. for 8 hours. To the reaction mixture, 200 ml of chloroform was added, and the mixture was washed with 70 ml of a 2N sodium hydroxide aqueous solution and then with an aqueous sodium chloride solution. The chloroform solution was distilled, and the residue was purified by silica gel column chromatography (CHCl$_3$/CH$_3$OH=9/1) to give 10.2 g (77%) of the above identified compound as an oily substance.

Rf value: 0.79 (CHCl$_3$/CH$_3$OH=9/1).

$^1$H-NMR(CDCl$_3$)δ value: 1.38(12H,m,CH$_3$×4), 1.82(4H,m,CH$_2$CHCH$_2$), 2.53(1H,m,CH$_2$CHCH$_2$), 3.14(4H,m,CH$_2$NCH$_2$), 3.43(1H,t,J=25.0Hz,NCH) , 4.25(8H,m,CH$_2$CH$_3$×4), 7.26 ( 5H,m, C$_6$H$_5$ ).

MS(EI): 447(M+), 310.

EXAMPLE 26

4-Phenylpiperidinomethylene bisphosphonic acid

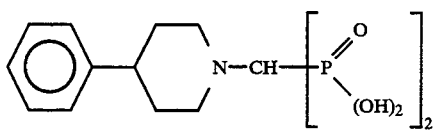

2.5 g (5.6 mmol) of 4-phenylpiperidinomethyl bisphosphonic acid ethyl ester obtained in Example 25 was added to 150 ml of concentrated hydrochloric acid, and the mixture was stirred for 10 hour at 100° C. The reaction solution was distilled under reduced pressure, and the residue was recrystallized from methanol to give 1.5 (78%) of the above identified compound as colorless crystals.

mp: 247°–249° C.

$^1$H-NMR(D$_2$O)δ value: 2.12(4H,m,CH$_2$CHCH$_2$), 2.96(1H,m,CH$_2$CHCH$_2$), 3.26(1H,t,J=18.2Hz,NCH), 3.82(4H,m,CH$_2$NCH$_2$), 7.41(5H,m,C$_6$H$_5$) (as sodium salt).

MS(EI): Not detected.

EXAMPLE 27

4-Benzylpiperidinomethylene bisphosphonic acid ethyl ester

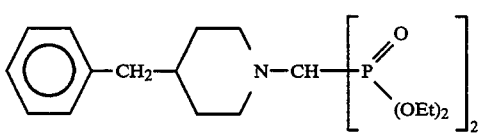

10.0 g (57.1 mmol) of 4-benzylpiperidine, 11.0 g (74.3 mmol) of HC(OEt)$_3$ and 28.0 g (203 mmol) of (EtO)$_2$PHO were reacted in the same manner as in Example 25 to give 19.3 g (69.4%) of the above identified compound as an oily substance.

Rf value: 0.83 (CHCl$_3$/CH$_3$OH=9/1).

$^1$H-NMR(CDCl$_3$)δ value: 1.34(12H,m,CH$_3$×4), 1.63(4H,m,

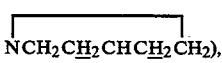

2.50(2H,d,J×16Hz,C$_6$H$_5$CH$_2$),
2.73(1H,m,CH$_2$CHCH$_2$), 2.97(4H,m,CH$_2$NCH$_2$), 3.36(1H,t,J=25.0Hz,NCH), 4.20(8H,m,CH$_2$CH$_3$×4), 7.19(5H,m,C$_6$H$_5$).

MS(EI): 413(M+) , 276.

EXAMPLE 28

4-Benzylpiperidinomethylene bisphosphonic acid

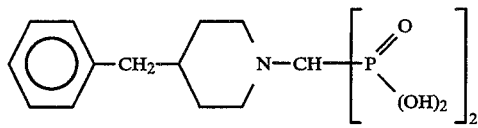

3.0 g (7.3 mmol) of 4-benzylpiperidinomethylene bisphosphonic acid ethyl ester obtained in Example 27 was added to 130 ml of concentrated hydrochloric acid, and 1.8 g (71.2%) of the above identified compound was obtained as colorless crystals in the same manner as in Example 26.

mp: 266°–269° C.

$^1$H-NMR(D$_2$O)δ value:

1.56(2H,m,NCH$_2$C$\underline{H}_2$CHCH$_2$CH$_2$), 1.90(1H,m,NCH$_2$CH$_2$C$\underline{H}$CH$_2$CH$_2$), 1.96(2H,m,NCH$_2$CH$_2$CHC$\underline{H}_2$CH$_2$), 2.64(2H,d,J=15Hz,C$\underline{H}_2$C$_6$H$_5$),
3.21(1H,t,J=18.0Hz,$\overline{\text{NCH}}$), 3.66(4H,m,CH$_2$NCH$_2$),
7.36(5H,m,C$_6$H$_5$), (as sodium salt).

MS(EI): Not detected.

EXAMPLE 29

4-Carbamoyl-4-(1-piperidyl)piperidinomethylene bisphosphonic acid ethyl ester

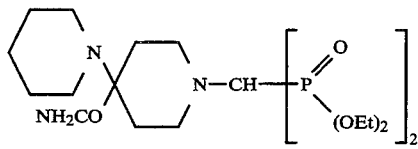

4.3 g (30 mmol) of 4-carbamoyl-4-(1-piperidyl)piperidine, 3.7 g (36 mmol) of HC(OEt)$_3$ and 8.6 g (93 mmol) of (EtO)$_2$PHO were reacted in the same manner as in Example 25 to give 16.2 g (66%) of the above identified compound as crystals.

mp: 192.0°–193.5° C.

$^1$H-NMR(CDCl$_3$)δ value: 1.35(12H,m,CH$_2$CHc×4), 1.50(6H,m,

NCH$_2$C$\underline{H}_2$C$\underline{H}_2$CH$_2$), 1.83(4H,m,NC$\underline{H}_2$CH$_2$CC$\underline{H}_2$CH$_2$), 2.52(4H,m,NC$\underline{H}_2$CH$_2$CH$_2$C$\underline{H}_2$), 1.30(4H,m,NC$\underline{H}_2$CH$_2$CCH$_2$C$\underline{H}_2$), 3.39(1H,t,J=20.0Hz,NCH), 4.21(8H,m,C$\underline{H}_2$CH$_3$×4),
6.55(2H,br s,NH$_2$).

MS(EI): 453(M+-NH$_2$CO), 316.

EXAMPLE 30

4-Carbamoyl-4-(1-piperidyl)piperidinomethylene bisphosphonic acid

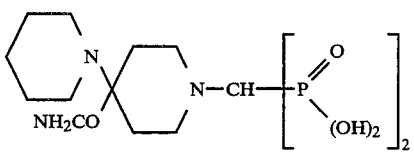

5.0 g of 4-carbamoyl-4-(1-piperidyl)piperidinomethylene bisphosphonic acid ethyl ester obtained in Example 29 was added to 200 ml of concentrated hydrochloric acid, and 2.7 g (70%) of the above identified compound was obtained as colorless crystals in the same manner as in Example 26.

mp: at least 280° C.

$^1$H-NMR(D$_2$O) δ value: 1.55(6H,m

NCH$_2$C$\underline{H}_2$C$\underline{H}_2$CH$_2$CH$_2$), 1.82(4H,m,NCH$_2$C$\underline{H}_2$CC$\underline{H}_2$CH$_2$), 2.57(4H,m,NC$\underline{H}_2$CH$_2$CH$_2$CH$_2$C$\underline{H}_2$),
3.40 (1H,t,J = 18.0 Hz,NCH), 3.82(4H,m,NC$\underline{H}_2$CH$_2$CCH$_2$C$\underline{H}_2$), (as sodium salt).
MS(EI): Not detected.

EXAMPLE 31

4,4-Difluoropiperidinomethylene bisphosphonic acid ethyl ester

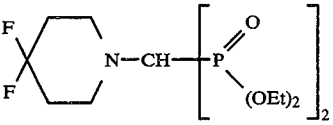

A mixture comprising 3.2 g (20.3 mmol) of 4,4-difluoropiperidine hydrochloride, 5.7 ml (60.6 mmol) of (C$_2$H$_5$)$_3$, 6.8 ml (60.3 mmol) of CH(EtO)$_3$ and 15 ml (120 mmol) of (EtO)$_2$POH, was reacted in the same manner as i Example 25 to give 5.8 g (70%) of the above identified compound as an oily substance.

Rf value: 0.46 (CHCl$_3$/CH$_3$OH=40/1).

$^1$H-NMR(CDCl$_3$)δ value: 1.36(12H,m,CH$_3$×4), 1.96(4H,m,CH$_2$CCH$_2$), 3.11(4H,m,CH$_2$NCH$_2$), 3.42(1H,t,J=25.0Hz,NCH), 4.22(8Hm,CH$_2$×4)

MS(EI): 407(M$^+$), 270.

EXAMPLE 32

4,4-Difluoropiperidinomethylene bisphosphonic acid

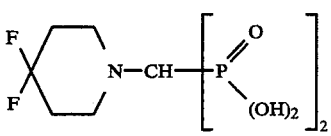

150 ml of concentrated hydrochloric acid was added to 1.0 g (2.45 mmol) of 4,4-difluoropiperidinomethylene bisphosphonic acid obtained in Example 31, and the mixture was reacted in the same manner as in Example 26 to give 0.4 g (55%) of the above identified compound as colorless crystals.

mp: 218°–220° C.
$^1$H-NMR(D$_2$O)δ value: 2.42(4H,m,CH$_2$CCH$_2$), 3.50(1H,t,J=17.0Hz,NCH), 3.89(4H,m,CH$_2$NCH$_2$), (as sodium salt).
MS(FAB): 294(M-H)$^-$, 278.

EXAMPLE 33

4-Chloro-4-methylpiperidinomethylene bisphosphonic acid

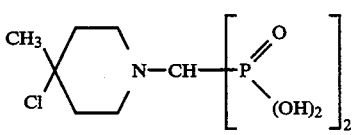

7.6 g (20 mmol) of 4-methylidenepiperidinomethylene bisphosphonic acid ester was dissolved in 250 ml of CH$_2$Cl$_2$, and the solution was stirred at a temperature of from 20° to 25° C. for 15 hours while blowing hydrogen chloride gas thereinto. The reaction solution was concentrated under reduced pressure, and to the residue, 150 ml of CCl$_4$ was added, and 17.0 g (85 mmol) of (CH$_3$)$_3$SiI was added thereto at 0° C. The mixture was stirred at room temperature for 5 hours. Then, the reaction solution was concentrated under reduced pressure. The residue was recrystallized from methanol to give 2.3 g (37%) of the above identified compound as colorless crystals.

mp: 217° 220° C.
$^1$H-NMR(D$_2$O)δ value: 1.71(3H,s,CH$_3$), 2.33(4H,m,CH$_2$CCH$_2$), 3.53(4H,m,CH$_2$NCH$_2$), 3.67(1H,t,J=15.0Hz,NCH) (as sodium salt).
MS(FAB): 294(M-H)$^-$, 276.

EXAMPLE 34

4-Hydroxy-4-methylpiperidinomethylene bisphosphonic acid

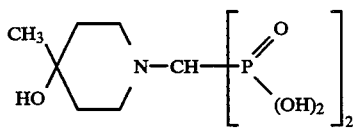

5.0 g (18.4 mmol) of 4-methylidenepiperidinomethylene bisphosphonic acid was added to 120 ml of 10% H$_2$SO$_4$, and the mixture was stirred for 45 hours at 100° C. The reaction solution was distilled under reduced pressure, and the precipitated powder was recrystallized from H$_2$O/C$_2$H$_5$OH to give 3.8 g (72%) of the above identified compound as colorless crystals.

mp: 232.0°–234.0° C.
$^1$H-NMR(D$_2$O)δ value: 1.33(3H,s,CH$_3$), 1.93(4H,m,CH$_2$CCH$_2$), 3.26(1H,t,J=19.0Hz,NCH), 3.71(4H,m,CH$_2$NCH$_2$), (as sodium salt).
MS(FAB): 290(M+H)$^+$.

EXAMPLE 35

4-Hexyl-4-hydroxypiperidinomethylene bisphosphonic acid

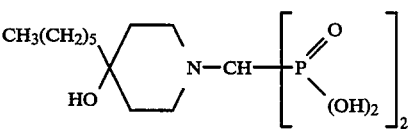

The reaction was conducted in the same manner as in Example 34 except that 3.4 g (10 mmol) of 4-hexylidenepiperidinomethylene bisphosphonic acid was used, to give 2.6 g (72.0%) of the above identified compound as colorless crystals.

mp: 258°–260° C.
$^1$H-NMR(D$_2$O)δ value: 0.85(3H,m,CH$_3$), 1.19–1.43(8H,m,CH$_2$CH$_2$CH$_2$CH$_2$CH$_3$), 1.82–1.95(2H,m,CCH$_2$CH$_2$CH$_2$) 3.18(1H,t,J=18.2Hz,NCH), 3.43–3.57(4H,m,

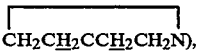
CH$_2$CH$_2$CCH$_2$CH$_2$N), 3.85–4.12(4H,m,CH$_2$NCH$_2$) (as sodium salt).
MS(FAB): 404(M+H)$^+$, 382.

EXAMPLE 36

4-Ethyl-4-hydroxypiperidinomethylene bisphosphonic acid

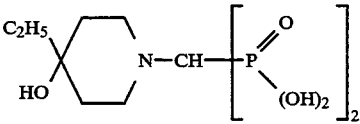

The reaction was conducted in the same manner as in Example 34 except that 3.4 g (12 mmol) of 4-ethylidenepiperidinomethylene bisphosphonic acid was used, whereby 2.9 g (81%) of the above identified compound was obtained as colorless crystals.

mp: 245°–247° C.
$^1$H-NMR(D$_2$O) δ value: 0.92(3H,t,J=8.1Hz,CH$_3$), 1.57(2H,q,J=8,1Hz,CH$_2$CH$_3$), 1.83–1.95(4H,m,

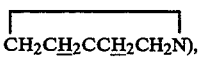
CH$_2$CH$_2$CCH$_2$CH$_2$N), 1.34(1H,t,J=18.0Hz,NCH), 3.51–3.65(2H,m, two H among CH$_2$NCH$_2$), 3.80–4.10(2H,m, two H among CH$_2$NCH$_2$) (as sodium salt).
MS(FAB): 304(M+H)$^+$, 286.

EXAMPLE 37

4-Fluoro-4-methylpiperidinomethylene bisphosphonic acid ethyl ester

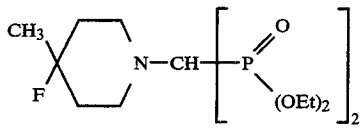

43 g (0.11 mol) of 4-oxopiperidinomethylene bisphosphonic acid ethyl ester was dissolved in 500 mt of dried tetrahydrofuran, and 250 ml (0.25 mol) of a methyl magnesium bromide solution in tetrahydrofuran (concentration: 1 mol/) was added thereto. The mixture was stirred at 25° C. for 2 hours, then subjected to post treatment and purified by column chromatography (SiO$_2$, cyclohexane/CHCl$_3$=1/1) to give 30.7 g (68.5%) of 4-hydroxy-4-methylpiperidinomethylene bisphosphonic acid ethyl ester as an oily substance. To 15.8 g (39.5 mmol) of this ester, 7.6 g (47.2 mmol) of diethylaminosulfur trifluoride was added at −78° C. in CH$_2$Cl$_2$, and the mixture was stirred at room temperature for 5 hours. The reaction solution was purified by column chromatography (SiO$_2$, hexane/isopropylether=5/1) to give 6.3 (40%) of the above identified compound.

$^1$H-NMR(CDCl$_3$) δ value: 1.28–1.40(12H,m,CH$_3$CH$_2$×4), 1.32(3H,d,CH$_3$), 1.53–1.92(4H,m,—CH$_2$CCH$_2$—), 2.87–2.96(2H,m,CH$_2$N), 3.11–3.26(2H,m,CH$_2$N), 3.40(1H,t,J=25Hz,NCH), 4.12–4.28 (8H,m,CH$_3$CH$_2$×4).

EXAMPLE 38

4-Fluoro-4-methylpiperidinomethylene bisphosphonic acid

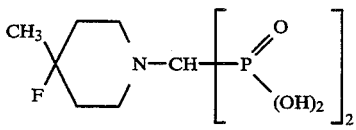

6.4 g (15.2 mmol) of 4-fluoro-4-methylpiperidinemethylene bisphosphonic acid ethyl ester obtained in Example 37 was dissolved in 300 ml of CCl$_4$, and 13 g (64.0 mmol) of trimethylsilyl iodide was added thereto at 5° C. The mixture was stirred at room temperature for 2 hours. Then, the solvent was distilled off under reduced pressure, and ethanol was added to the residue, followed by stirring overnight. The reaction solution was treated to give 4.1 g (94.0%) of the above identified compound as a colorless powder.

mp: 241.0°–245.0° C.

$^1$H-NMR(D$_2$O)δ value: 1.33(3H,d,J=22.0Hz,CH$_3$), 1.87–2.22(4H,m,CH$_2$CCH$_2$), 3.23(1H,t,J=18.0Hz,NCH), 3.53(2H,m,NCH$_2$), 3.93(2H,m,NCH$_2$), (as sodium salt).

MS(FAB): 286(M-H)$^-$.

EXAMPLE 39

4-Cyano-4-phenylpiperidinomethylene bisphosphonic acid ethyl ester

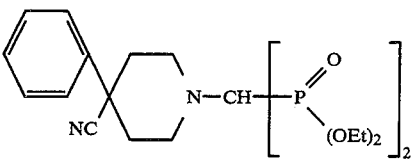

mp: 191°–193° C.

$^1$H-NMR(CDCl$_3$) δ value: 1.35–1.44(12H,m,CH$_3$×4), 1.98–2.20(4H,m,3-,5-CH$_2$), 3.20–3.48(4H,m,2-,6-CH$_2$), 3.45(1H,t,J=25Hz,NCH), 4.17–4.33(8H,m,CH$_3$CH$_2$×4), 7.25–7.53(5H,m,phenyl H).

MS: 422(M+).

EXAMPLE 40

4-Carbamoyl,4-phenylpiperidinomethylene bisphosphonic acid

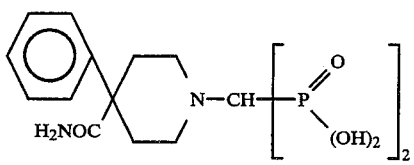

mp: at least 280° C.

$^1$H-NMR(D$_2$O) δ value: 2.02–2.92(4H,m,3-,5-,CH$_2$), 3.30(1H,t,J=17Hz,NCH) 3.65–3.94(4H,m,2-,6-CH$_2$), 7.31–7.55(5H,m,phenyl).

MS(FAB.): 377(M-H)$^-$.

EXAMPLE 41

4-Piperidinopiperidinomethylene bisphosphonic acid ethyl ester

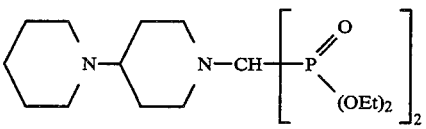

Rf value: 0.32 (CHCl$_3$/CH$_3$OH=10/1).

$^1$H-NMR(CDCl$_3$) δ value: 1.31–1.39(12H,m,CH$_3$×4), 1.41–198(10H,m,3-,5-,3'-,4'-,5'-CH$_2$), 2.30–3.22(9H,m,2-,6-,2'-,6'-CH$_2$and 4-CH), 3.37(1H,t,J=24Hz,NCH), 4.13–4.27(8H,m,CH$_3$CH$_2$×4).

MS: 455(M+).

EXAMPLE 42

4-Piperidinopiperidinomethylene bisphosphonic acid

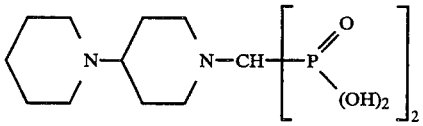

mp: 257°–260° C.

¹H-NMR(D₂O)δ value 1.35–2.52(10H,m,3-,5-,3'-,4'-,5'-CH₂), 3.06(1H,t,J=15Hz,NCH), 3.51–3.94(9H,m,2-,6-,2'-,6'-CH₂ and 4-CH).
MS(FAB): 341[M-H]⁻.

EXAMPLE 43

4-Hydroxypiperidinomethylene bisphosphonic acid ethyl ester

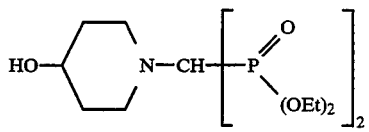

Rf value: 0.66 (CHCl₃/CH₃OH=9/1).
¹H-NMR(CDCl₃)δ value 1.31–1.39(12H,m,CH₃×4), 1.46–1.94(4H,m,3-5-CH₂), 2.19(1H,br s,OH), 2.87–3.17(4H,m,2-,6-CH₂), 3.37(1H,t,J=25Hz,NCH), 3.61–3.72(1H,m,4-CH), 4.13–4.27(8H,m,CH₃C$\underline{H}$₂×4).
MS: 387(M+).

EXAMPLE 44

4-Hydroxypiperidinomethylene bisphosphonic acid

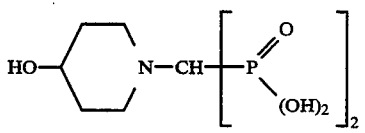

mp: 250°–252° C.
¹H-NMR(D₂₃O) δ value: 1.71–2.26(4H,m,3-,5-CH₂), 3.32(1H,t,J=17Hz,NCH), 3.50–4.09(5H,m,2-,6-CH₂ and 4-CH)
MS(FAB): 274[M-H]⁻.

EXAMPLE 45

4-Azidopiperidinomethylene bisphosphonic acid ethyl ester

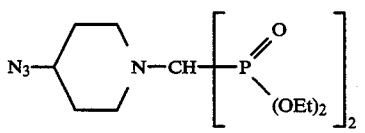

Rf value: 0.78 (CHCl₃/CH₃OH=9/1).
¹H-NMR(CDCl₃) δ value: 1.30–1.39(12H,m,CH₃×4), 1.50–1.96(4H,m,3-,5-CH₂), 2.88–3.22(4H,m,2-,6-CH₂), 3.31–3.45(1H,m,4-CH), 3.35(1H,t,J=25Hz,NCH), 4.12–4.27(8H,m,CH₃C$\underline{H}$₂×4)
MS: 412 (M+).

EXAMPLE 46

4-Azidopiperidinomethylene bisphosphonic acid

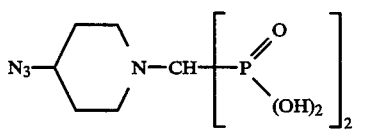

mp: 274°–276° C.

¹H-NMR(D₂O) δ value: 1.82–2.31(4H,m,2-,6-CH₂), 3.29(1H,t,J=17Hz,NCH), 3.50–3.97(5H,m,3-,5-CH₂ and 4-CH).
MS(FAB): 299[M-H]⁻.

EXAMPLE 47

4-Hydroxy-4-vinylpiperidinomethylene bisphosphonic acid ethyl ester

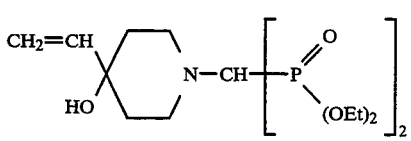

Rf value: 0.21 (CHCl₃/CH₃OH=20/1).
¹H-NMR(CDCl₃) δ value: 1.36(12H,t,J=7Hz,CH₃×4), 1.54–1.80(4H,m,3-,5-CH₂), 2.90–3.28(4H,m,2-,6-CH₂), 3.40(1H,t,J=25Hz,NCH), 4.12–4.28(8H,m,CH₃C$\underline{H}$₂×4), 5.07{1H,d,J=10Hz,C$\underline{H}$₂=(cis H)}, 5.27{1H,d,J=16Hz,CH₂=(trans H)}, 5.95(1H,q,J=16,10Hz,=CH).
MS: 413(M+).

EXAMPLE 48

4-Hydroxy-4-vinylpiperidinomethylene bisphosphonic acid

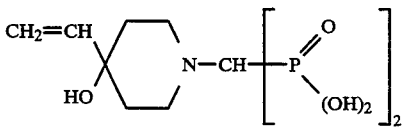

mp: 239°–241° C.
¹H-NMR(D₂O) δ value: 1.82–2.22(4H,m,3-,5-CH₂), 3.46–4.22(4H,m,2-,6-CH₂), 3.62(1H,t,J=18Hz,NCH), 5.17{1H,d,J=10Hz,CH₂=(cis H)}, 5.30{1H,d,J=16Hz,CH₂=(trans H)}, 5.97(1H,q,J=10,16Hz,CH=).
MS(FAB): 300[M-H]⁻.

EXAMPLE 49

4-Allyl-4-hydroxypiperidinomethylene bisphosphonic acid ethyl ester

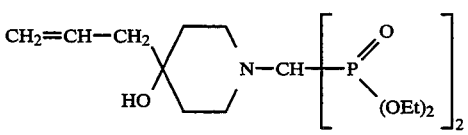

Rf value: 0.47 (CHCl₃/CH₃OH=10/1).
¹H-NMR(CDCl₃) δ value: 1.35(12H,t,J=7Hz,CH₃×4), 1.52–1.67(4H,m,3-,5-CH₂), 2.23(2H,d,J=7Hz,C$\underline{H}$₂CH=), 2.90–3.33(4H,m,2-,6-CH₂), 3.39(1H,t,J=25Hz,NCH), 4.15–4.27(8H,m,CH₃C$\underline{H}$₂×4), 5.13{1H,d,J=14Hz,C$\underline{H}$₂=(trans H)}, 5.17{1H,d,J=8Hz,CH₂=(cis H)}, 5.80–5.96(1H,m,—CH).
MS: 427 (M+).

EXAMPLE 50

4-Allyl-4-hydroxypiperidinomethylene bisphosphonic acid

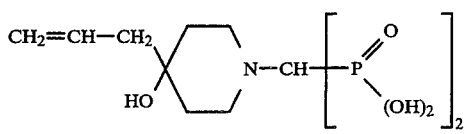

mp: 236°–238° C.
$^1$H-NMR(D$_2$O) δ value: 1.85–2.10(4H,m,3-,5-CH$_2$), 2.29(2H,d,J=8Hz,CHCH$_2$), 3.45–4.14(4H,m,2-,6-CH$_2$), 3.65(1H,t,J=18Hz,NCH),
5.16{1H,d,J=1Hz,=CH$_2$(trans H)},
5.21{1H,d,J=9Hz,=CH2(cis H)},
5.81–5.96(1H,m,=CH).
MS(FAB).: 314[M-H]$^-$.

EXAMPLE 51

4-Hydroxy-4-isopropylpiperidinomethylene bisphosphonic acid ethyl ester

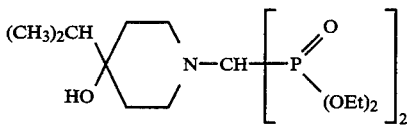

Rf value: 0.28 (CHCl$_3$/CH$_3$OH=20/1).
$^1$H-NMR(CDCl$_3$) δ value: 0.91{6H,d,J=7Hz,(CH$_3$)$_2$CH},
1.34(12Hz,t,J=7Hz,CH$_3$CH$_2$×4), 1.47–1.67{4H,m,3-,5-CH$_2$, (CH$_3$)$_2$CH}, 2.87–3.27(4H,m,2-,6-CH$_2$), 3.38(1H,t,J=25Hz,NCH),
4.13–4.27(8H,m,CH$_3$CH$_2$×4).
MS: 429 (M+)

EXAMPLE 52

4-Hydroxy-4-isopropylpiperidinomethylene bisphosphonic acid

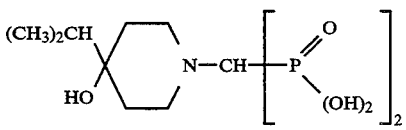

$^1$H-NMR(D$_2$O) δ value 0.90{6H,d,J=7Hz,(CH$_3$)$_2$CH},
1.64–1.76{1H,m,(CH$_3$)$_2$CH}, 1.84–1.96(4H,m,3-,5-CH$_2$), 3.14 ( 1H, t ,J=18Hz ,NCH) , 3.78–4.06 ( 4H,m, 2-,6-CH$_2$ ) .

EXAMPLE 53

4-t-Butyl-4-hydroxypiperidinomethylene bisphosphonic acid ethyl ester

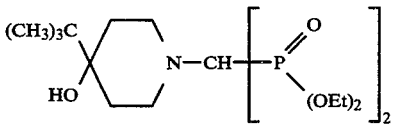

Rf value: 0.49 (CHCl$_3$/CH$_3$OH=10/1).

$^1$H-NMR(CDCl$_3$) δ value: 0.92{9H,s,(CH$_3$)$_3$C}, 1.35(12H,t,J=7Hz,CH$_3$CH$_2$×4), 1.45–1.80(4H,m,3-,5-CH$_2$), 2.86–3.24(4H,m,2-,6-CH$_2$), 3.38(1H,t,J=25Hz,NCH),
4.09–4.27(8H,m,CH$_3$CH$_2$×4).
MS: 443 (M+).

EXAMPLE 54

4-t-Butyl-4-hydroxypiperidinomethylene bisphosphonic acid

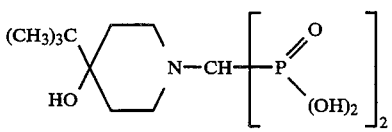

mp: 251°–254° C.
$^1$H-NMR(D$_2$O) δ value: 0.81{9H,s, (CH$_3$)$_3$C}, 1.72–2.00(4H,m,3-,5-CH$_2$) , 3.07(1H,t,J=17Hz,NCH), 3.29–3.39(2H,m,ax H of 2-,6-CH$_2$), 3.82–3.95(2H,m,equ H of 2-,6-CH$_2$).
MS(FAB): 330[M-H]$^-$.

EXAMPLE 55

3-Dimethylaminopyrrolidylmethylene bisphosphonic acid ( ethyl ester

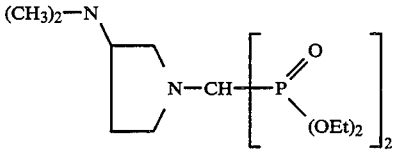

Rf value: 0.15 (CHCl$_3$/CH$_3$OH=20/1).
$^1$H-NMR(CDCl$_3$) δ value: 1.32–1.42(12H,t,J≦12Hz,CH$_3$CH$_2$×4),
1.73–2.07(2H,m,4-CH$_2$), 2.29(6H,s,NCH$_3$×2),
2.83–3.57(5H,m,2-,4-CH$_2$,3-CH),
3.63(1H,t,J=25Hz,NCH),
4.14–4.29(8H,m,CH$_3$CH$_2$×4).
MS: 400 (M+).

EXAMPLE 56

3-Dimethylaminopyrrolidylmethylene bisphosphonic acid

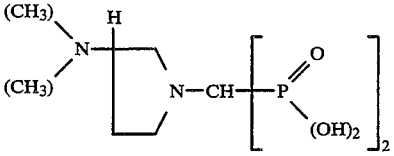

$^1$H-NMR(D$_2$O) δ value: 2.20–3.10(2H,mr4-CH$_2$), 3.00(6H,s,CH$_3$×2), 4.61(5H,m,2-,5-CH$_2$, 3-CH), 3.63(1H,t,J=17Hz,NCH).
MS(FAB): 287[M-H]$^-$.

EXAMPLE 57

Preparation of 3,3-dimethylpiperidinomethylene bisphosphonic acid ethyl ester

A mixture comprising of 3,3-dimethylpiperidine, 19 g of diethyl phosphite and 7.8 g of HC(OEt)$_3$, was treated in the same manner as in Example 1 to give 15.2 of the above identified compound as an oily substance.

Rf value: 0.88 (silicagel plate, chloroform/methanol (10/1)).

$^1$H-NMR(CDCl$_3$): δ value, 0.92{6H,s,(CH$_3$)$_2$C}, 1.18–1.26(2H,m,4-CH$_2$), 1.37(12H,m,CH$_2$CH$_3$×4), 1.51–1.60(2H,m,5-CH$_2$), 1.62–1.66(2H,s,2-CH$_2$), 1.89–1.97(2H,m,6-CH$_2$), 3.33(1H,t,J=25Hz,NCH), 4.08–4.27(8H,m,CH$_2$CH$_3$×4).

MS(EI): 400(M$^+$+1), 262.

EXAMPLE 58

Preparation of 3,3-dimethylpiperidinomethylene bisphosphonic acid

A mixture comprising 8 g of 3,3-dimethylpiperidinomethylene bisphosphonic acid ethyl ester obtained in Example 57 and 80 ml of 12N hydrochloric acid, was treated in the same manner as in Example 2 to give 1.5 g of the above identified compound.

mp: 226°–229° C.

$^1$H-NMR(D$_2$O): δ value, 1.04(3H,s,CH$_3$), 1.10(3H,s,CH$_3$), 1.32–1.63(2H,m,4-CH$_2$), 1.81–2.05(2H,m,5-CH$_2$), 3.24(1H,t,J=18Hz,NCH), 3.21–3.46(2H,m,2-CH$_2$), 3.48–3.65(2H,m,6-CH$_2$).

MS(FAB): [M-H]$^-$286.

EXAMPLE 59

Preparation of 4,4-dimethylpiperidinomethylene bisphosphonic acid ethyl ester

A mixture comprising 8 g of 4,4-dimethylpiperidine, 55 g of diethyl phosphite and 19 g of HC(OEt)$_3$, was reacted in the same manner as in Example 1 to give 19 g of the above identified compound as an oily substance.

Rf value: 0.87 (silicagel plate, chloroform/methanol (10/1)).

$^1$H-NMR(CDCl$_3$): δ value, 0.91(6H,s,CH$_3$×2), 1.32–1.41(16H,m,CH$_3$CH$_2$×4,3-,5-CH$_2$), 2.95–3.01(4H,m,2-,6-CH$_2$), 3.38(1H,t,J=25Hz,NCH), 4.15–4.28(8H,m,CH$_3$CH$_2$×4).

MS(EI): 399(M+), 262.

EXAMPLE 60

Preparation of 4,4-dimethylpiperidinomethylene bisphosphonic acid

A mixture comprising 10 g of 4,4-dimethylpiperidinomethylene bisphosphonic acid ethyl ester obtained in Example 59 and 80 ml of 12N hydrochloric acid, was treated in the same manner as in Example 2 to give 4.0 g of the above identified compound as a colorless crystalline powder.

mp: 168°–170° C.

$^1$H-NMR(D$_2$O): δ value, 1.04(6H,s,CH$_3$×2), 1.65–1.78(4H,m,3-,5-CH$_2$), 3.31(1H,t,J=1SHz,NCH), 3.35–4.03(4H,m,2-,6-CH$_2$),

MS(FAB): 286 [M-H]$^-$.

EXAMPLE 61

Preparation of 4-oxopiperidinomethylene bisphosphonic acid ethyl ester and 4-oxopiperidinomethylene bisphosphonic acid A mixture comprising 50 g (0.35 mol) of 1,4-dioxa-8-azaspiro[4,5]-decane, 62 g (0.42 mol) of CH(OEt)$_3$ and 150 g (1.1 mol) of diethyl phosphite, was stirred at 140° C. for 12 hours. Then, the reaction solution was extracted with chloroform, and the extract was washed with a 2N sodium hydroxide aqueous solution. Then, the chloroform layer was dried, and chloroform was distilled off to give 130 g of crude 1,4-dioxa-8-azaspiro[4,5]-decane-8-methylene bisphosphonic acid ethyl ester as an oily substance.

$^1$H-NMR(CDCl$_3$) δ value: 1.39(12H,t,J=7Hz,CH$_3$×4) 2.42–2.48(4H,m,3-,5-CH$_2$), 3.28–3.36(4H,m,2-,6-CH$_2$), 3.52(1H,t,J=25Hz,NCH), 4.26–4.29(SH,m,CH$_3$CH$_3$CH$_2$×4).

MS: 429(M+), 292.

This oily substance was stirred at 110° C. in 500 ml of an aqueous acetic acid solution (400 ml of acetic acid + 100 ml of water). Then, the residue obtained by removing the aqueous acetic acid solution from the reaction solution, was purified by silica gel column chromatography (2% ethanol/chloroform) to give 95 g (yield: 70%) of 4-oxopiperidinomethylene bisphosphonic acid ethyl ester.

Rf value: 0.63 (silicagel plate, chloroform/methanol (10/1).

$^1$H-NMR(CDCl$_3$) δ value: 1.35(12H,t,J=7Hz,CH$_3$×4), 1.68–1.75(4H,m,3-,5-CH$_2$), 3.05–3.13(4H,m,2-,6-CH$_2$), 3.41(1H,t,J=25Hz,NCH), 3.94(4H,s,OCH$_2$CH2), 4.13–4.30(SB,m,CH$_3$CH$_2$×4).

MS: 386(M+), 248.

7.7 g of 4-oxopiperidinomethylene bisphosphonic acid ethyl ester and 12 ml of trimethylsilyl iodide (specific gravity: 1.41) were stirred at 0° C. for 30 minutes in 120 ml of CCl$_4$. Then, the reaction solution was distilled under reduced pressure. To the residue, 50 ml of water and 200 ml of CH$_3$OH were added, and the mixture was stirred at a temperature of from 25 to 30° C. for 5 hours. The reaction solution was distilled, and the residue was purified by silica gel column chromatography (chloroform/methanol=9/1) to give 2.0 g (yield: 37%) 4-oxopiperidinomethylene bisphosphonic acid.

mp: 260°–264° C.

$^1$H-NMR(D$_2$O) δ value: 2.06'2.17(4H,m,3-,5-CH$_2$), 3.52–3.71(4H,m,2-,6-CH$_2$), 3.72(1H,t,J=25Hz,NCH).

MS(FAB): 272[M-H]$^-$.

TEST EXAMPLES FOR PHARMACOLOGICAL ACTIVITIES

Now, the test method with respect to the antihypercalcemic activities of the compounds of the present invention by using rats having the thyroid gland and the pala thyroid gland removed, and the results will be described.

Wister male rats of 7 weeks old (150–170 g) were anesthetized with nenbutal, and the thyroid gland and the pala thyroid gland were surgically removed by the method disclosed by Russel R. G. et al, Calcif. Tissue, Res., 183–196 (1970) and by Muehlbauer R. C. et al, Mineral Electrolyte Metab., 5 296–300 (1981). After the operation, the rats were fed on normal food for three days, and on the fourth day, the blood was sampled, and the serum calcium value was measured by an atomic absorption method, whereby rats having the serum calcium value lowered to a level of from 5 to 7 mg/de were selected.

These rats were divided into groups so that each group consisted of five rats. A compound of the present invention was dissolved in a 0.5% CMC aqueous solution or physiological saline and adjusted for administration at a dose of 10 mg/kg. Such a solution was subcutaneously administered at a dose of 2 ml/kg once a day for three days. To a control group, a 0.5% CMC aqueous solution or physiological saline was administered. Next day, 0.2 ml of the blood was sampled, and the serum calcium value was measured in the same manner as described above (this value was designated as 0 day value (a)).

At the same time, an osmotic pump (2001 Model, manufactured by Alza Co.) having parathyroid hormone (PTH) (50 μg/0.2 ml physiological saline) sealed in, was subcutaneously embedded on the back of each rat, and 24 hours later, the blood was sampled from the aorta abdominalis, whereupon the serum calcium value was measured (this value was designated as one day value (b)).

From the obtained results, the serum increased calcium value was calculated by the following formula:

Serum increased calcium value = one day value (b) − 0 day value (a)

The results obtained by the above test are shown in Tables 3, 4 and 5.

TABLE 3

| Compound | Dose (mg/kg) | Serum calcium value (μg/ml) 0 day value (a) | 1 day value (b) | Serum increased calcium value [(b)−(a)] |
|---|---|---|---|---|
| Example 2 | 10 | 47.2 ± 2.22 | 109.0 ± 8.47 | 61.8 ± 7.38 |
| Example 4 | 10 | 51.4 ± 7.23 | 128.7 ± 3.31 | 77.3 ± 6.37 |
| Example 6 | 10 | 40.3 ± 3.61 | 90.6 ± 5.30 | 50.3 ± 6.25 |
| Example 8 | 10 | 47.1 ± 4.17 | 109.8 ± 2.07 | 62.7 ± 4.27 |
| Example 10 | 10 | 45.5 ± 5.54 | 108.8 ± 6.80 | 63.3 ± 1.91 |
| Example 12 | 10 | 53.9 ± 7.82 | 138.9 ± 4.29 | 85.0 ± 6.27 |
| Example 58 | 10 | 50.8 ± 2.35 | 130.4 ± 7.57 | 79.6 ± 7.07 |
| Example 60 | 10 | 46.5 ± 8.69 | 110.4 ± 1.59 | 63.9 ± 2.15 |
| CMC (control) | | 61.4 ± 0.87 | 255.0 ± 12.45 | 193.8 ± 12.17 |

TABLE 4

| Compound | Dose (mg/kg) | Serum calcium value (μg/ml) 0 day value (a) | 1 day value (b) | Serum increased calcium value [(b)−(a)] |
|---|---|---|---|---|
| Example 14 | 10 | 60.99 ± 2.67 | 68.34 ± 2.94 | 7.35 ± 2.65 |
| Example 16 | 10 | 52.12 ± 1.86 | 53.30 ± 4.89 | 1.18 ± 3.70 |
| Example 18 | 10 | 61.34 ± 7.49 | 66.05 ± 6.68 | 4.72 ± 4.05 |
| Example 20 | 10 | 63.02 ± 3.75 | 71.73 ± 6.32 | 8.71 ± 2.72 |
| Example 21 | 10 | 60.87 ± 5.61 | 65.92 ± 7.91 | 5.05 ± 3.19 |
| Physiological saline (control) | | 75.05 ± 8.09 | 120 ± 5.32 | 45.07 ± 9.49 |

TABLE 5

| Compound | Dose (mg/kg) | Serum calcium value (μg/ml) 0 day value (a) | 1 day value (b) | Serum increased calcium value [(b) − (a)] |
|---|---|---|---|---|
| Example 27 | 10 | 66.2 ± 3.13 | 79.5 ± 2.77 | 13.3 ± 1.62 |
| Example 29 | 10 | 66.7 ± 5.91 | 74.8 ± 1.82 | 8.1 ± 4.35 |
| Example 31 | 10 | 65.3 ± 3.15 | 73.1 ± 3.96 | 7.8 ± 3.57 |
| Example 33 | 10 | 52.1 ± 1.73 | 53.3 ± 4.91 | 1.2 ± 3.77 |
| Example 34 | 10 | 61.0 ± 2.82 | 68.3 ± 2.87 | 7.4 ± 2.69 |
| Example 35 | 10 | 70.8 ± 3.85 | 84.5 ± 6.73 | 13.7 ± 4.13 |
| Example 37 | 10 | 53.8 ± 2.10 | 55.7 ± 3.63 | 1.9 ± 3.10 |
| Example 54 | 10 | 67.3 ± 2.83 | 77.0 ± 3.74 | 9.7 ± 5.32 |
| CMC (control) | | 75.1 ± 8.09 | 140.1 ± 6.51 | 65.0 ± 8.36 |
| APD (Comparative drug) | 10 | 60.2 ± 8.32 | 83.6 ± 3.13 | 23.4 ± 6.50 |

APD: Pamidoronate

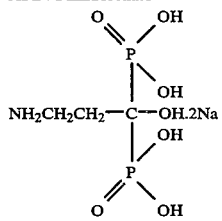

From the above results, it is apparent that the compounds of the present invention strongly suppress the increase of the serum calcium value by administration of PTH. Accordingly, it is apparent that they inhibit bone resorption activities by PTH.

In this test for pharmacological activities, no side effect such as inflammation of the skin was observed in any one of the rats to which the bisphosphonic acid derivatives of the present invention were subcutaneously administered.

TEST EXAMPLE FOR TOXICITY $LD_{50}$ of the compounds of Examples 2, 14, 16, 18, 33, 34 and 58 was at least 100 mg/kg when subcutaneously injected to ddy mice (male) of five weeks old (22–27 g).

Now, formulation examples of the compounds of the present invention will be described.

FORMULATION EXAMPLE 1 (TABLETS)

Tablets each containing 100 mg of the active ingredients, were prepared in accordance with the following formulation.

| Components | Amount (mg) |
|---|---|
| Compound of Example 2 | 100 |
| Crystalline cellulose | 50 |
| Carboxymethyl cellulose | 10 |
| Calcium lauryl sulfate | 1 |
| Methyl cellulose | 3 |
| Calcium stearate | 4 |

FORMULATION EXAMPLE 2 (CAPSULES)

200 mg of a mixture containing 100 mg of an active ingredient per capsule was packed in a capsule in accordance with the following formulation to give capsules.

| Components | Amount (mg) |
|---|---|
| Compound of Example 4 | 100 |
| Lactose | 50 |
| Corn starch | 40 |
| Crystalline cellulose | 50 |
| Calcium stearate | 2 |

We claim:

1. A bisphosphonic acid derivative of the formula (I) or a pharmaceutically acceptable salt thereof:

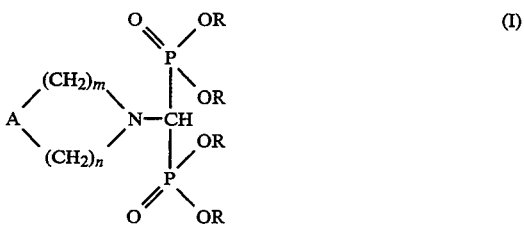

wherein A is

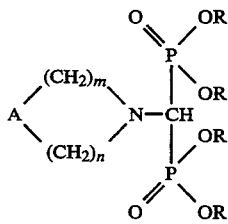

wherein each of $R^5$ and $R^6$, which are the same or different, is a hydroxyl group, a halogen atom, a cyano group, a carbamoyl group, a $C_{7-15}$ aralkyl group, a phenyl group, a mono-halogenated phenyl group, a mono-$C_{1-6}$ alkyl substituted phenyl group, an amino group, a $C_{1-6}$ alkylamino group, a di-$C_{1-6}$ alkylamino group, a $C_{1-6}$ alkoxyamino group, a di-$C_{1-6}$ alkoxyamino group, a $C_{2-6}$ alkenyl group, a $C_{2-6}$ alkynyl group or a piperidino group;

each of m and n is 0 or a positive integer, provided that (m+n) is from 3 to 5; and R is a hydrogen atom, a $C_{1-8}$ alkyl group or a $C_{7-15}$ aralkyl group.

2. A bisphosphonic acid derivative of the formula (I) or a pharmaceutically acceptable salt thereof:

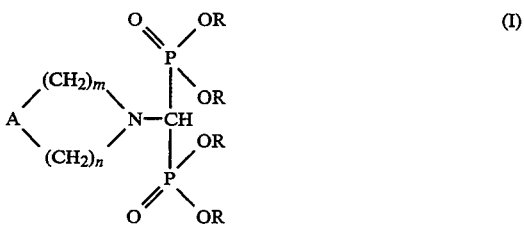

wherein A is

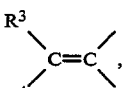

or

wherein, each of $R^3$ and $R^4$, which are the same or different, is (i) a hydrogen atom, (ii) a $C_{1-6}$ alkyl group, a $C_{2-6}$ alkenyl group, a $C_{2-6}$ alkynyl group, a $C_{1-6}$ alkyl-carbonyl group, a $C_{2-6}$ alkenyl-carbonyl group, or a $C_{2-6}$ alkynyl-carbonyl group, wherein each of these groups are unsubstituted or substituted with one or two substituents selected from the group consisting of an amino group, a $C_{1-6}$ alkylamino group, a di-$C_{1-6}$ alkylamino group, a halogen atom and a carboxyl group, or (iii) a halogen atom, each of m and n is 0 or a positive integer, provided that (m+n) is from 2 to 5; and R is a hydrogen atom, a $C_{1-8}$ alkyl group or a $C_{7-15}$ aralkyl group.

3. The compound according to claim 2, which is 4-methylidenepiperidino-methylene bisphosphonic acid.

4. The compound according o claim 2, which is 4-ethylidenepiperidinomethylene bisphosphonic acid.

5. The compound according to claim 2, which is 4-hexylidenepiperidinomethylene bisphosphonic acid.

6. The compound according to claim 1, which is a 4-fluoro-4-methylpiperidinomethylene bisphosphonic acid.

7. The compound according to claim 2, which is 4-butylidenepiperidinomethylene bisphosphonic acid.

8. A bone resorption inhibitor composition comprising an effective amount of the compound of claim 1 or 2 and a pharmaceutically acceptable carrier or diluent.

9. A method for treating osteoporosis comprising administering an effective amount of a compound according to claim 1 or 2.

10. The compound according to claim 1 or 2, wherein the $C_{7-15}$ aralkyl group is selected from the group consisting of benzyl, phenyl, phenylethyl and phenylmethyl.

* * * * *